(12) United States Patent
Kennedy et al.

(10) Patent No.: US 9,182,371 B2
(45) Date of Patent: Nov. 10, 2015

(54) MICROSCALE WESTERN BLOT

(75) Inventors: Robert Kennedy, Ann Arbor, MI (US); Gwendolyn Anderson, Brunswick, ME (US)

(73) Assignee: The Regents Of The University Of Michigan, Ann Arbor, MI (US)

( * ) Notice: Subject to any disclaimer, the term of this patent is extended or adjusted under 35 U.S.C. 154(b) by 499 days.

(21) Appl. No.: 13/592,933

(22) Filed: Aug. 23, 2012

(65) Prior Publication Data

US 2013/0213811 A1 Aug. 22, 2013

Related U.S. Application Data

(63) Continuation-in-part of application No. PCT/US2011/026312, filed on Feb. 25, 2011.

(60) Provisional application No. 61/308,330, filed on Feb. 26, 2010.

(51) Int. Cl.
  *G01N 27/447* (2006.01)
  *G01N 33/543* (2006.01)

(52) U.S. Cl.
  CPC .... *G01N 27/44739* (2013.01); *G01N 33/54386* (2013.01)

(58) Field of Classification Search
  CPC ............................ G01N 27/447–27/453; B01L 3/5027–3/502792
  See application file for complete search history.

(56) References Cited

U.S. PATENT DOCUMENTS

| | | | |
|---|---|---|---|
| 5,580,434 A * | 12/1996 | Robotti et al. | ............... 204/451 |
| 6,632,655 B1 | 10/2003 | Mehta et al. | |
| 2004/0048360 A1 | 3/2004 | Wada et al. | |
| 2006/0192107 A1 * | 8/2006 | DeVoe et al. | ............... 250/288 |

FOREIGN PATENT DOCUMENTS

WO    WO-2009/067521 A1    5/2009

OTHER PUBLICATIONS

International Search Report and Written Opinion dated Aug. 1, 2012 in corresponding PCT International Patent Application No. PCT/US2011/026312 (eight pages).
Anderson, G.J. et al., "Western Blotting Using Capillary Electrophoresis", Anal. Chem., Feb. 15, 2011 83(4), pp. 1350-1355.

* cited by examiner

*Primary Examiner* — J. Christopher Ball
(74) *Attorney, Agent, or Firm* — Harness, Dickey & Pierce, PLC

(57) ABSTRACT

Systems and methods are provided for integrating the electrophoresis and blotting of samples. A capillary electrophoresis and blotting system allows concomitant electrophoretic separation and blotting to provide a rapid and simplified process. A microfluidic electrophoresis and blotting system provides electrophoretic separation in a microfluidic channel followed by electroblotting from the microfluidic channel to also provide a rapid and simplified process. These systems and methods can be used to assay smaller amounts of sample in less time than conventional processes, including conventional Western blotting techniques.

38 Claims, 16 Drawing Sheets

MICROSCALE WESTERN BLOT

CROSS-REFERENCE TO RELATED APPLICATIONS

Figure 1:
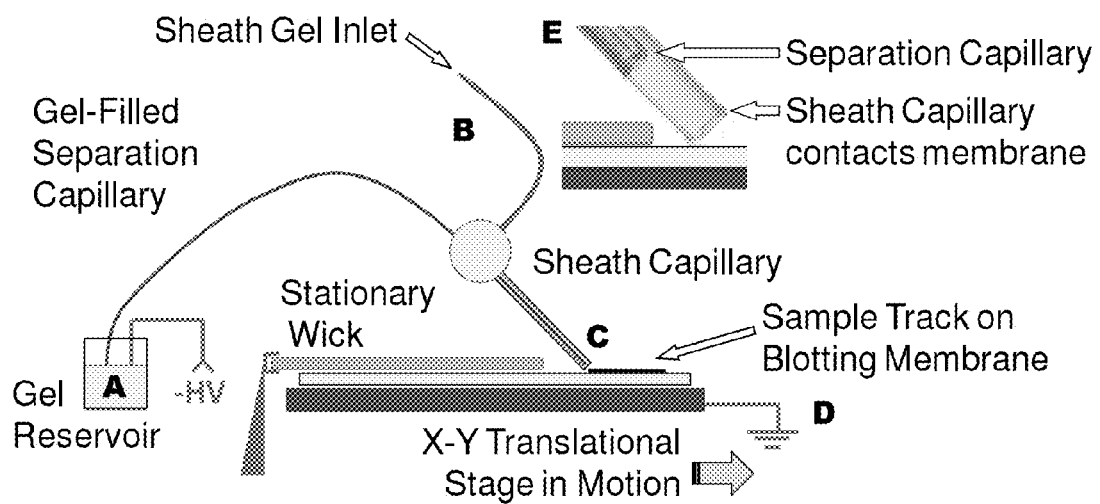

This application is a continuation-in-part of International Application No. PCT/US2011/026312, filed Feb. 25, 2011, which claims the benefit of and priority to U.S. Provisional Application No. 61/308,330, filed on Feb. 26, 2010. The entire disclosures of the above applications are incorporated herein by reference.

GOVERNMENT RIGHTS

This invention was made with U.S. Government support under Grant Nos. CHE-0809013 and CHE-0514638 awarded by the National Science Foundation. The U.S. Government has certain rights in the invention.

FIELD

The present technology relates to electrophoresis and blotting systems including capillaries or microfluidic channels.

INTRODUCTION

Affinity interactions coupled with separation methods are important techniques for life science research and biotechnology. Affinity chromatography, Southern blotting, and gel-mobility shift assays are examples of widely used techniques that combine separation methodology with selective binding to improve information content and selectivity. Of the techniques that combine separations and affinity interactions, Western blotting is perhaps the most widely used. The method is routinely used to assay proteins in complex mixtures and frequently used as a confirmatory test for clinical assays and regulatory tests.

In a Western blot, proteins are separated by size using sodium dodecyl sulfate-polyacrylamide gel electrophoresis (SDS-PAGE) and then transferred to a membrane by electro-blotting (Towbin et al., *Proc. Natl. Acad. Sci. U.S.A.* 1979, 76, 4350-4354; Burnette, W. N., *Anal. Biochem.* 1981, 112, 195-203; Gong et al., *IEEE Sens. J.* 2008, 8, 601-607). The membrane is treated with blocking protein and then probed sequentially with primary and secondary antibody (conjugated with a label) to detect target protein. The technique is powerful because it provides selective protein detection based on size and antibody binding in a semi-quantitative assay. The method is also characterized by simplicity, reliability, and facile methods development.

Despite the great utility of Western blots, they have several well-known limitations. Western blots are manually intensive and time-consuming, generally requiring anywhere from 4 to 24 h when taking into account gel preparation, separation, electro-blotting, and multiple incubations. Sensitivity is typically in the nanogram range making them incompatible with sample limited analysis. Analysis of large proteins is hindered by difficulty of transferring them from slab gels (Kurien et al., *Methods* 2006, 38, 283-293). Finally, the method has not been miniaturized, which wastes materials and reduces sensitivity.

Efforts have been made to improve Western blotting by reducing time and reagent requirements and introduce automation. A semi-automatic platform has been developed that uses vacuum filtration to pull blocking, antibody and reagent solutions through the membrane to decrease time required for the immunoassay procedure (SNAP i.d. Protein Detection System User Guide, available online at www.millipore.com/userguides/tech1/00103871 (accessed Jul. 1, 2010)). Microfluidics technology has been used to create flow channels for applying blocking and antibody solutions over the surface of the blot, which can be advantageous in reducing reagent consumption and optimizing conditions (Pan W Y, Chen W, Jiang X Y, *Anal. Chem.* 2010, 82, 3974-3976). These advances improve the immunoassay, but do not address other aspects of the Western such as separation and blotting. Another approach is integration of separation with faster blotting in a microfluidic format (He et al., *Anal. Chem.* 2009, 81, 8177-8184; He et al., *J. Am. Chem. Soc.* 2010, 132, 2512-2513). In this method, antibodies pre-immobilized in the chip selectively capture protein targets from a high-speed gel separation. In one example, 500 nM free prostate specific antigen was separated, transferred and blotted in <5 min with a signal-to-noise ratio of 40. This technique reduces timescales and offers potential for automation; but the requirements for microfabrication, pre-labeling analyte proteins with fluorophore, and pre-loading of antibody are barriers for many applications.

SUMMARY

The present technology includes systems, methods, articles, and compositions that relate to electrophoresis and blotting systems that include a capillary or microfluidic channel.

In some embodiments, a capillary electrophoresis and blotting system includes an electrophoresis component comprising a separation capillary having proximal and distal ends. The separation capillary is operable to be filled with a sieving medium, such as polyacrylamide, and electrophorese a sample from the proximal end to the distal end. The electrophoresis component of the system can also include a plurality of separating capillaries that can allow a plurality of samples to be run in parallel, for example. The system also includes a blotting component comprising a surface and a translating component. The translating component is operable to change position of the distal end of the separation capillary relative to the surface of the blotting component. The distal end of the separation capillary and the surface of the blotting component are operable to be electrically coupled during electrophoresis of the sample.

The capillary electrophoresis and blotting system can further comprise a buffer capillary having proximal and distal ends with the distal end of the buffer capillary located proximate to the distal end of the separation capillary. The buffer capillary is operable to be filled with electrophoresis buffer or gel to electrically couple the distal end of the separation capillary and the surface of the blotting component during electrophoresis of the sample. The capillary electrophoresis and blotting system can further comprise a pump operable to flow electrophoresis buffer or gel from the proximal end to the distal end of the buffer capillary. The buffer capillary can also comprise a sheath capillary that is coaxial to the separation capillary and the distal end of the buffer capillary can extend further than the distal end of the separation capillary toward the surface of the blotting component. Fluid in the sheath may be caused to flow towards the membrane, for example using a pump, to aid transfer of sample components migrating from the separation capillary to the membrane.

The system and the blotting component can further include various aspects. The surface of the blotting component can include a blotting membrane, such as polyvinylidene fluoride, nitrocellulose, or nylon. The system can also have a wick operable to wet the blotting membrane, for example, where the blotting membrane and the wick are wet with a solution comprising electrophoresis buffer and methanol. The wick can also be operable to wet a portion of the surface of the blotting membrane prior to the translating component positioning the distal end of the separation capillary at the portion of the surface of the blotting membrane. For example, the wick can be coupled to the translating component. In some cases, the membrane may be kept wet and electrically conducting by applying gel or electrophoresis buffer from a separate reservoir or spray nozzle. In some cases, the blotting membrane comprises a gel impregnated membrane, where the gel impregnated membrane can be used without a wick and/or without a buffer capillary. The fluid in the sheath capillary or the fluid used to wet the membrane can also include components that promote binding of the separated protein components to the membrane. These fluids can also include components that allow stable electrophoresis to be performed. For example, use of methanol and buffer mixtures on the membrane and sieving media in the sheath capillary allow stable electrophoresis and binding of sample proteins to the membrane.

The system can also include an assay component comprising a reagent capillary having proximal and distal ends where the reagent capillary is operable to be filled with a reagent and dispense the reagent from the distal end. In some cases, the distal end of the reagent capillary is operable to follow the distal end of the separation capillary when position of the distal end of the separation capillary is changed by the translation component. The assay component can also include a plurality of reagent capillaries including a first reagent capillary and a second reagent capillary. The distal end of the first reagent capillary can be operable to follow the distal end of the separation capillary when position of the distal end of the separation capillary is changed by the translation component and the distal end of the second reagent capillary can be operable to follow the distal end of the first reagent capillary. For example, the first reagent capillary can be filled with a blocking reagent and the second reagent capillary can be filled with a detecting reagent, such as an antibody.

In some embodiments, a capillary electrophoresis and blotting method includes providing an electrophoresis and blotting system as described. The separation capillary is filled with a sieving medium and the surface of the blotting component includes a blotting membrane. A sample is electrophoresed through the separation capillary from the proximal end to the distal end and the translating component is used to change position of the distal end of the separation capillary relative to the surface of the blotting component. The sample can include a protein and the protein can subsequently be detected on the blotting membrane using an immunoassay, for example.

In some embodiments, a microfluidic electrophoresis and blotting system is provided that includes an electrophoresis component and a blotting component. The electrophoresis component comprises a microfluidic channel having proximal and distal ends where the microfluidic channel is formed at least in part by two porous membranes, such as nanoporous membranes. In some cases, the electrophoresis component further comprises a plurality of microfluidic channels. The microfluidic channel is operable to be filled with a sieving medium and electrophorese a sample from the proximal end toward the distal end. The blotting component comprises a surface proximate to one of the porous membranes forming the microfluidic channel, where the surface can include a blotting membrane. The blotting component is operable to electrophorese the contents of the microfluidic channel toward the surface of the blotting component.

In some embodiments, a microfluidic electrophoresis and blotting method includes providing a microfluidic electrophoresis and blotting system as described. The microfluidic channel is filled with a sieving medium and the surface of the blotting component comprises a blotting membrane. A sample is electrophoresed through the microfluidic channel from the proximal end toward the distal end, which is then followed by electrophoresing the contents of the microfluidic channel toward the surface of the blotting component and the blotting membrane. The sample can include a protein and the protein can subsequently be detected on the blotting membrane using an immunoassay, for example.

In some embodiments, a microfluidic electrophoresis and blotting system comprises an electrophoresis component comprising a microfluidic channel and a post-column channel. The microfluidic channel has proximal and distal ends and is operable to be filled with a sieving medium and electrophorese a sample from the proximal end toward the distal end. The post-column channel has proximal and distal ends and operable to be filled with an electrophoresis buffer or gel. The distal end of the microfluidic channel is coupled to the proximal end of the post-column channel. The system includes a blotting component comprising a surface and a translating component operable to change position of the distal end of the post-column channel relative to the surface of the blotting component. The distal end of the post-column channel and the surface of the blotting component are operable to be electrically coupled during electrophoresis of the sample.

In some embodiments, a microfluidic electrophoresis and blotting method comprises providing a microfluidic electrophoresis and blotting system as described, wherein the microfluidic channel comprises a sieving medium, the post-column channel comprises an electrophoresis buffer or gel, and the surface of the blotting component comprises a blotting membrane. A sample is electrophoresed through the microfluidic channel from the proximal end toward the distal end, through the post-column channel from the proximal end toward the distal end, and toward the surface of the blotting component and the blotting membrane. The translating component is used to change position of the distal end of the post-column channel relative to the surface of the blotting component during electrophoresis.

The present systems offer substantial benefits over traditional blotting methods and systems, such as Western blotting methods and systems. Capillary gel electrophoresis allows for better separation at higher applied fields (e.g., 400 V/cm) than conventional gel electrophoresis. Furthermore, the system as a whole can largely automate Western blotting, improve throughput, and reduce sample and reagent consumption.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 1. Instrument overview. Sample is injected at the inlet (proximate end) of the separation capillary (A). The protein mixture migrates the gel-filled capillary under an electric field that is generated by the application of negative high voltage (A) and ground (D). Proteins exit the capillary at the distal end as it drags over the surface, and deposit on the blotting membrane (C). A translational stage moves the blot past the end of capillary to preserve the protein separation on the membrane. Gel pumped through a sheath capillary (B) that surrounds the latter portion of the separation capillary and makes direct contact with the blotting membrane (E). The blotting membrane (and wick overlay) are moistened with 50:50 (v:v) methanol:electrophoresis buffer.

Figure 2:
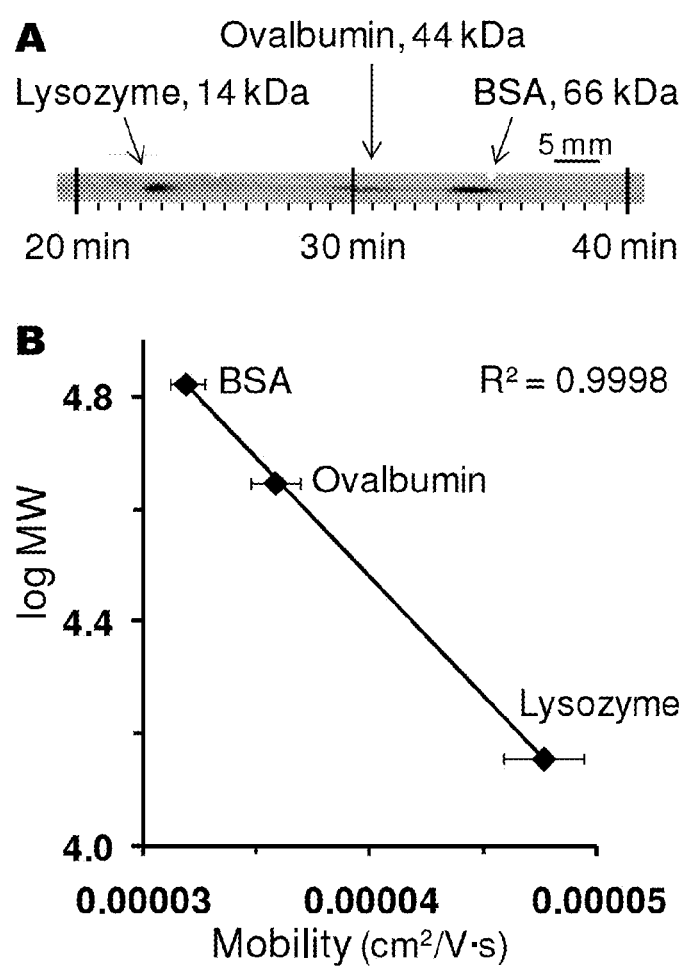

FIG. 2. Size-dependent separation of standard FITC-labeled proteins performed using system depicted in FIG. 1. (A) 3 proteins, prepared in stock samples of 100-300 µg/mL. The molecular weight for unlabeled protein is noted beside each observed peak. (B) Plotting log MW as a function of mobility yields a linear plot for these FITC-labeled proteins.

Figure 3:
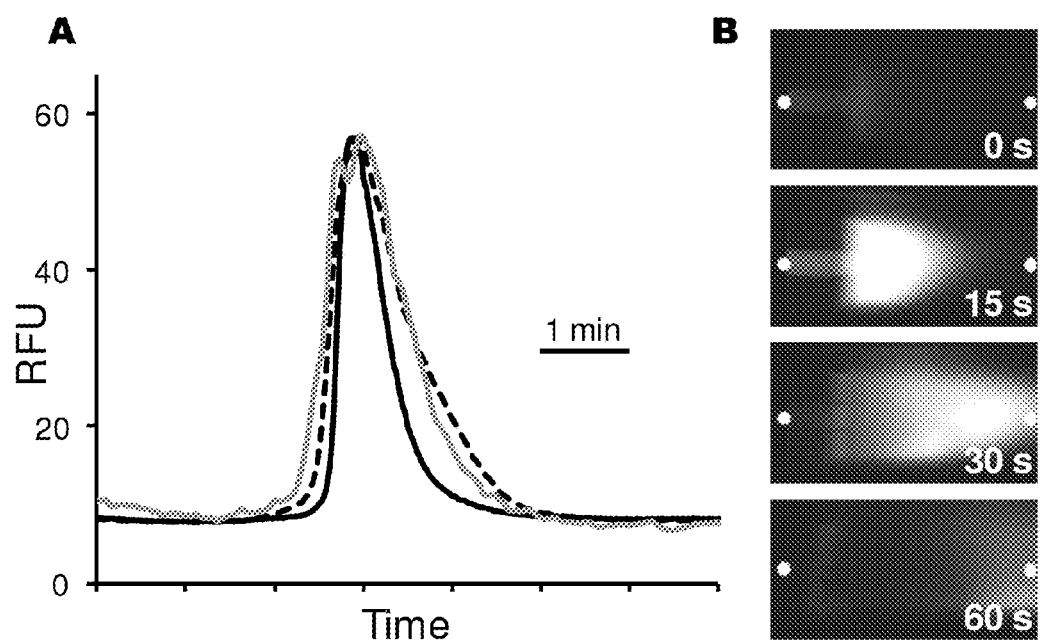

FIG. 3. Measurements of band broadening inside sheath capillary and on membrane. (A) Comparison of peak width for on-column detection (black line), in sheath 350 µm beyond the exit of the separation capillary (dashed line), and on membrane after traveling through 500 µm of sheath (gray line). The on-column and in sheath measurements were taken from the same separation. The membrane data was from a separate injection. All separations used 150 µg/mL FITC-BSA as the sample separated at 300 V/cm with an effective capillary length of 20 cm. Capillaries were not thermostatted. (B) Selected images of protein exiting the separation capillary and entering sheath capillary. Time zero represents time zone first appears at exit of separation capillary and is 32 minutes after sample injection. The white dots indicate where signal was measured to construct FIG. 3A.

Figure 4:
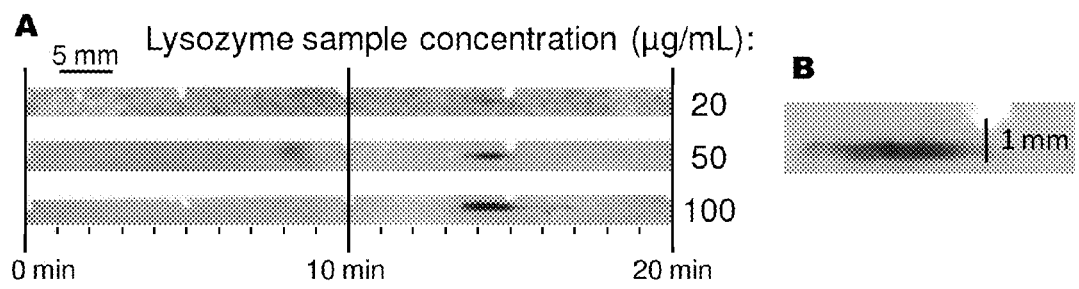

FIG. 4. Capillary electrophoresis-based Western blot of lysozyme at 3 different concentrations obtained using the system depicted in FIG. 1. Samples were separated at 300 V/cm and the resulting membranes probed with antibody using an automated system (Millipore Snap i.d.) for applying reagents. Analysis time for an individual assay was about 60 min. Enlargement shows that zones spread perpendicular to the deposition track. The sheath capillary was 250 µm in diameter but the zone is 450 µm wide.

Figure 5:
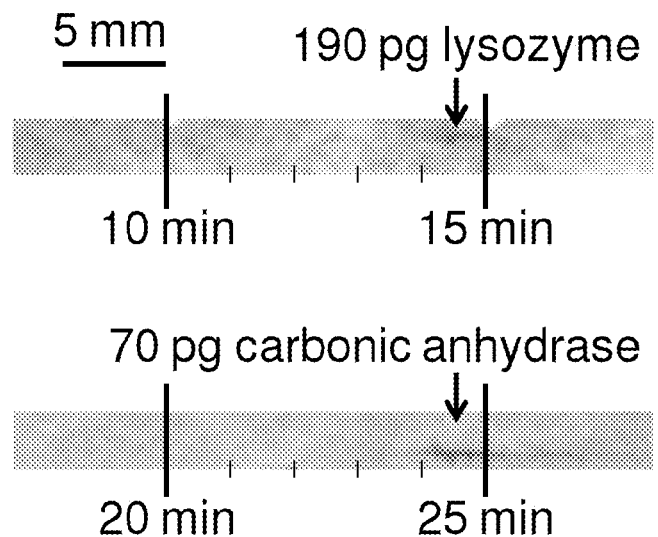

FIG. 5. CE-Western blot of unlabeled sample proteins at low levels obtained using the system depicted in FIG. 1 for separation and sample deposition. Estimated quantities of proteins calculated from injection length, elution time and sample concentrations are displayed for different proteins.

Figure 6:
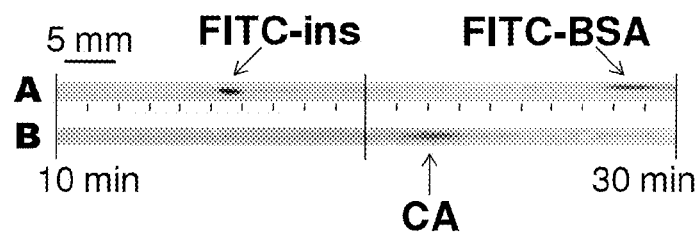

FIG. 6. Immunoassay of unlabeled peak with labeled size standards. (A) Initial fluorescence scan displays FITC-labeled size standards at approximately 16 and 28 minutes for insulin (FITC-ins) and bovine serum albumin (FITC-BSA). (B) Upon immunoassaying this PVDF membrane with anti-carbonic anhydrase IgG, the intermediate MW protein, carbonic anhydrase (CA), is detected at 22 minutes.

Figure 7:
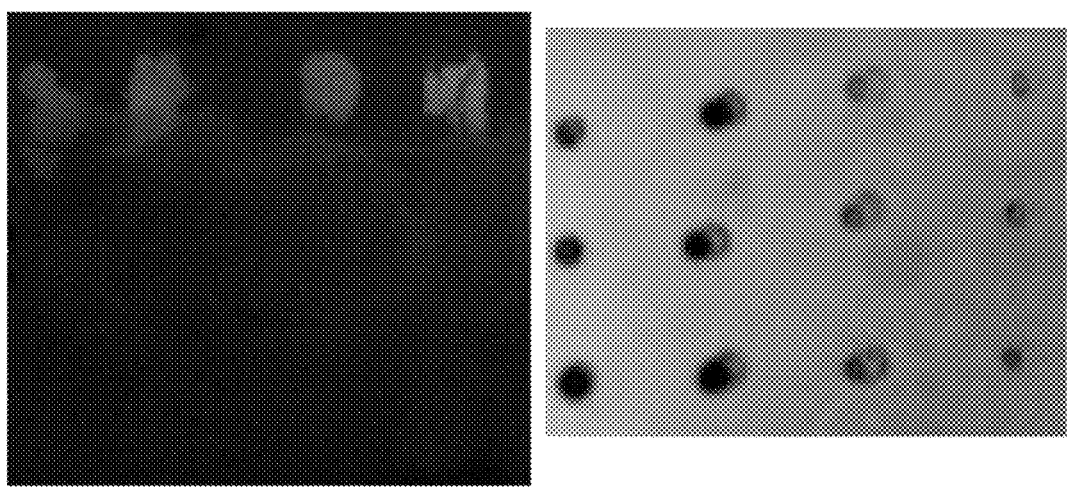

FIG. 7. Proteins spotted onto a PVDF membrane and detected by chemiluminescence (left) or fluorescence (right). On the left, protein samples containing SDS were spotted using a pipette onto a PVDF membrane soaked with aqueous electrophoresis buffer at progressively lower concentrations in 3 rows, only the top row is visible and those spots are spread out and not uniform. On the right, a similar experiment except the proteins were spotted onto a membrane wetted with 50% methanol 50% transfer buffer. The spots have sharp edges and clearly visible suggesting rapid and efficient capture. These results illustrate the importance of using a buffer/organic solvent mixture on the membrane.

Figure 8:
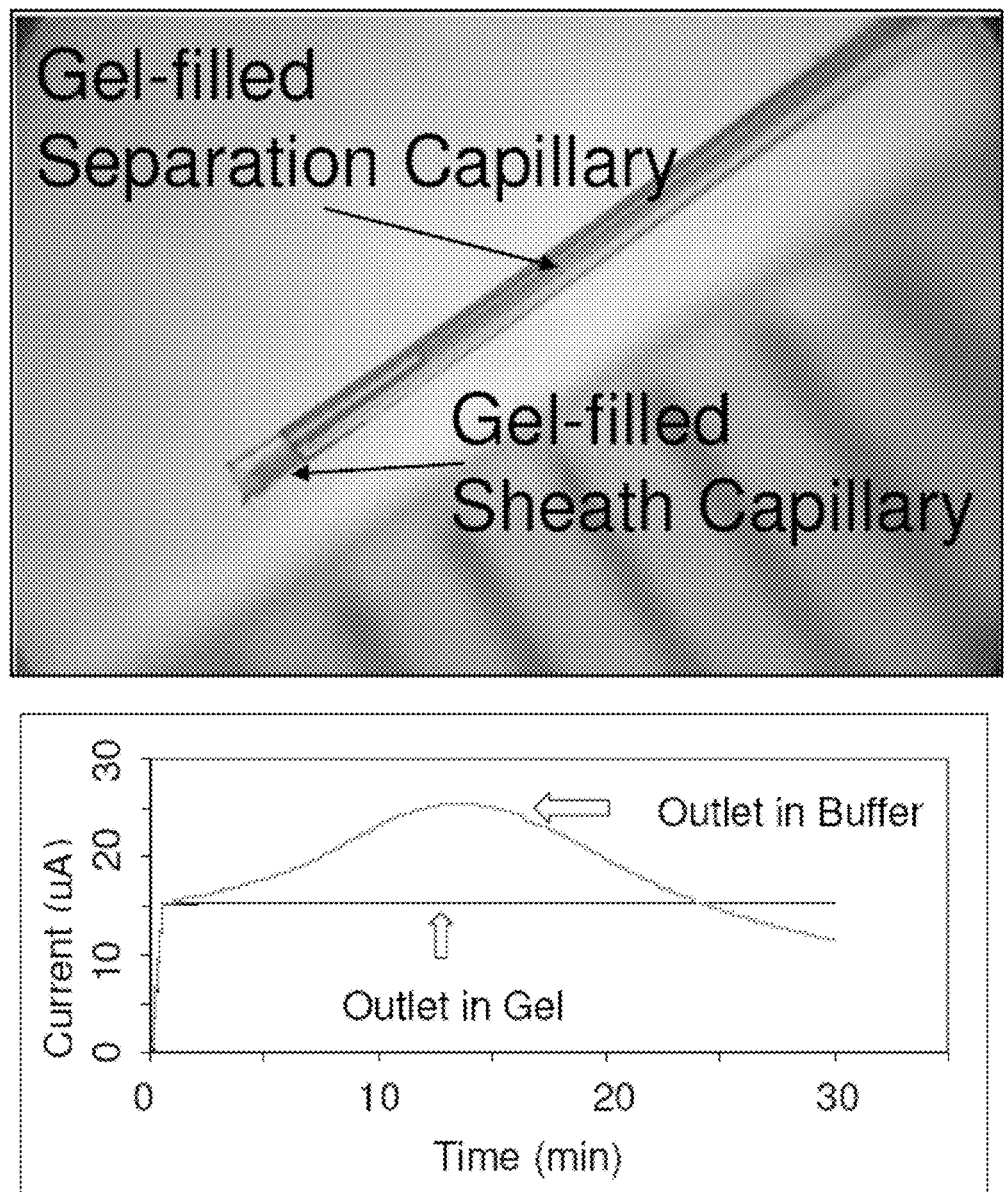

FIG. 8. Close up view of the sheath capillary arrangement used in the system shown in FIG. 1. The separation capillary is threaded through a second capillary that is filled with gel. The addition of this sheath capillary is different from previous use of capillary electrophoresis interfaced to membranes. Bottom graph depicts examples of current traces obtained with the sheath filled with buffer or with gel. Stable current with gel provides for good electrophoretic separation.

Figure 9:
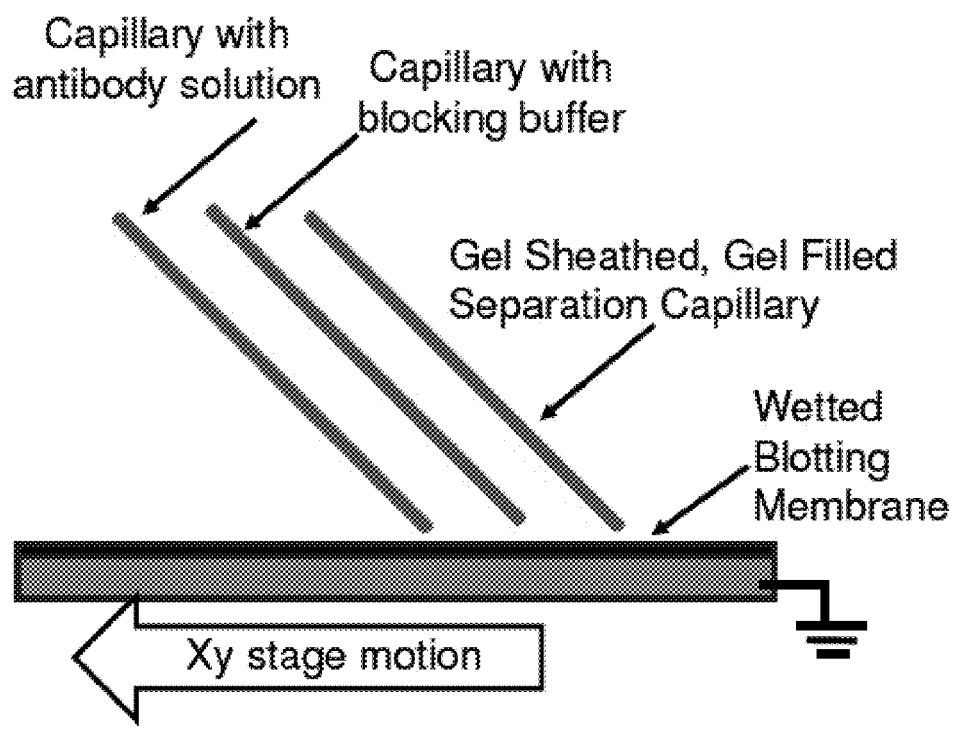

FIG. 9. An arrangement of capillaries that allows blocking buffer and antibody solution, as used in the immunoassay part of the Western blot, to be added to the membrane as separation is taking place. This triple capillary (more capillaries can be added if necessary) can be mounted as depicted by the capillary in FIG. 1. This arrangement allows more rapid microWestern blotting by simultaneously applying the necessary reagents with the capture of separated protein.

Figure 10:
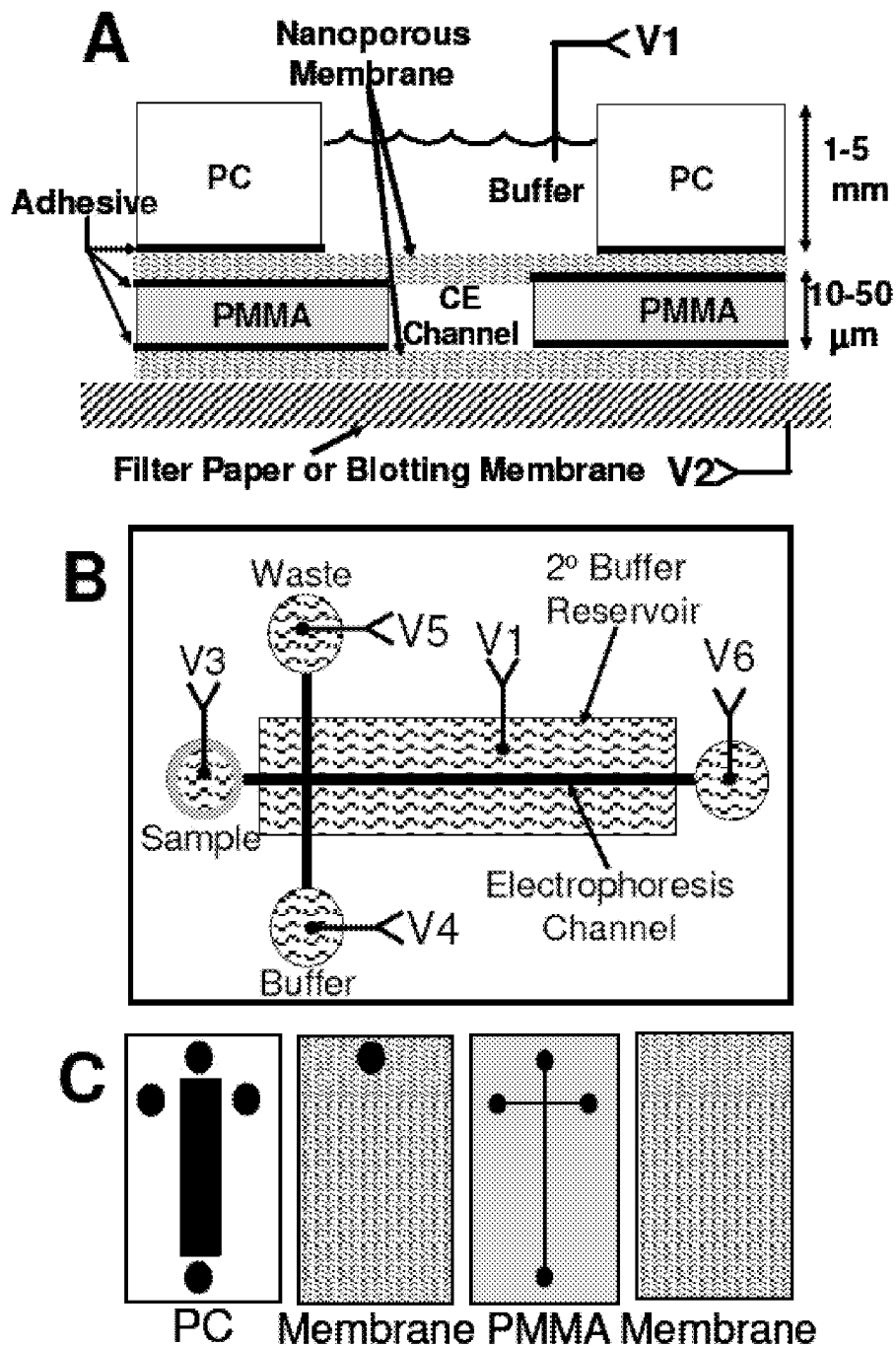

FIG. 10. Embodiment of a microfluidic laminated chip for Western blot. (A) Cross-section showing different layers. Separation occurs out of plane of the image, electrotransfer from top to bottom. (B) Top view shows channel layout (heavy black line), reservoirs, and voltage. (C) Shows the 4 layers laminated for the chip. Layers are arranged so that top to bottom in (A) is equivalent to left to right in (C). Blacked out regions are cut through the layers. PC is polycarbonate, PMMA is polymethylmethacrylate.

Figure 11:
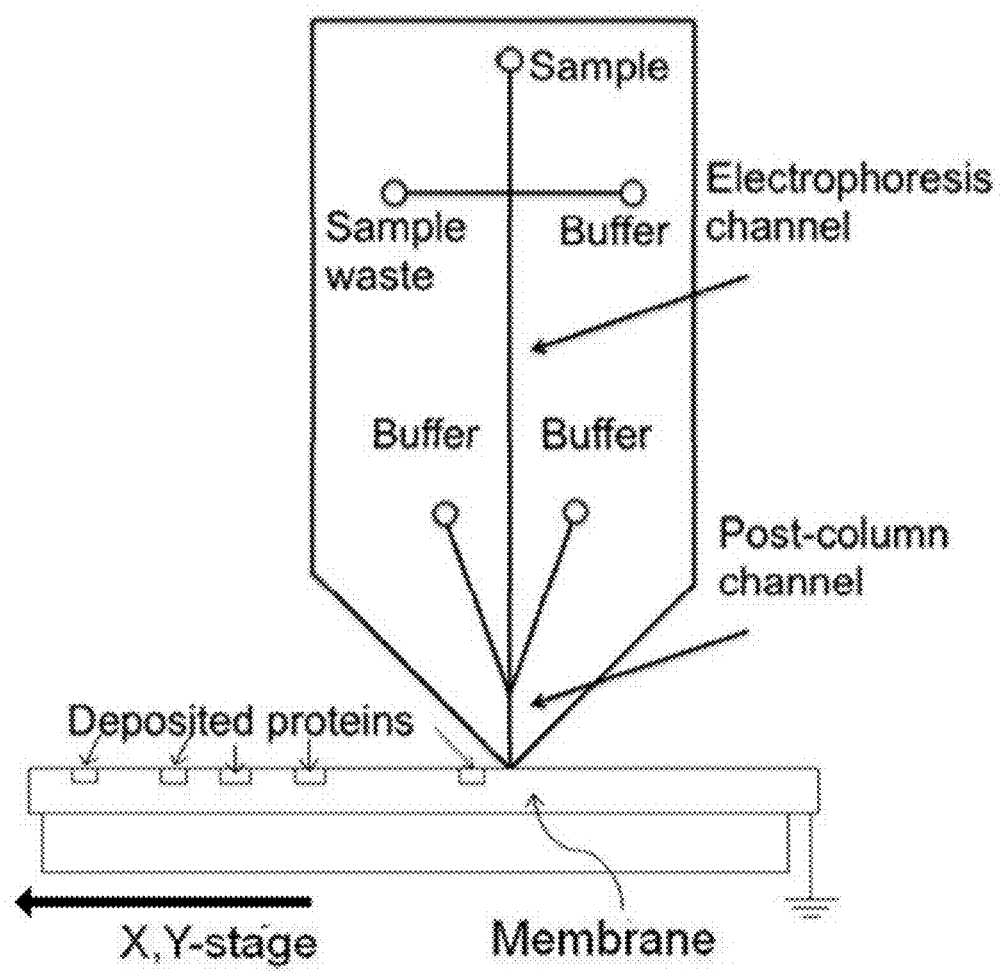

FIG. 11. Embodiment of a microfluidic chip based system with a moving membrane for electrophoresis and blotting. Reservoirs (shown as circles) can include Buffer (B), Sample (S), Sample Waste (SW), and post-column addition solution (P). Voltage is applied between B and the X, Y stage for separation.

Figure 12:
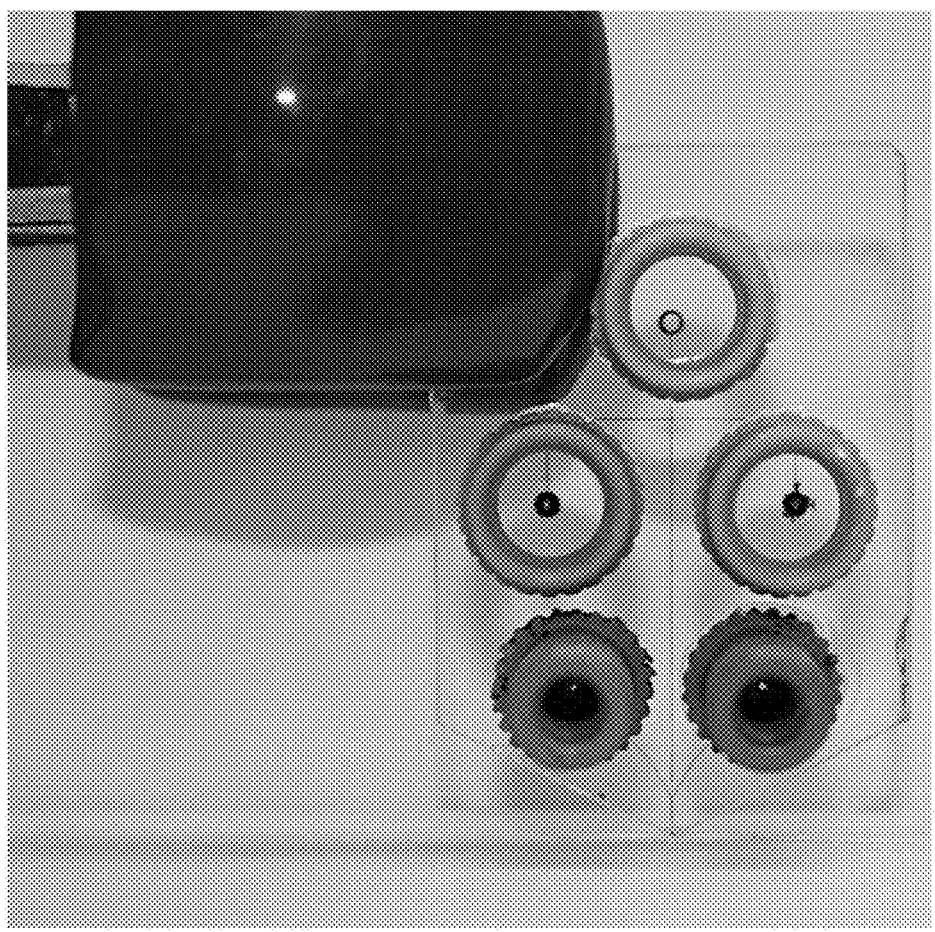

FIG. 12. Photograph of a microfluidic chip representing the embodiment shown in FIG. 11.

Figure 13:
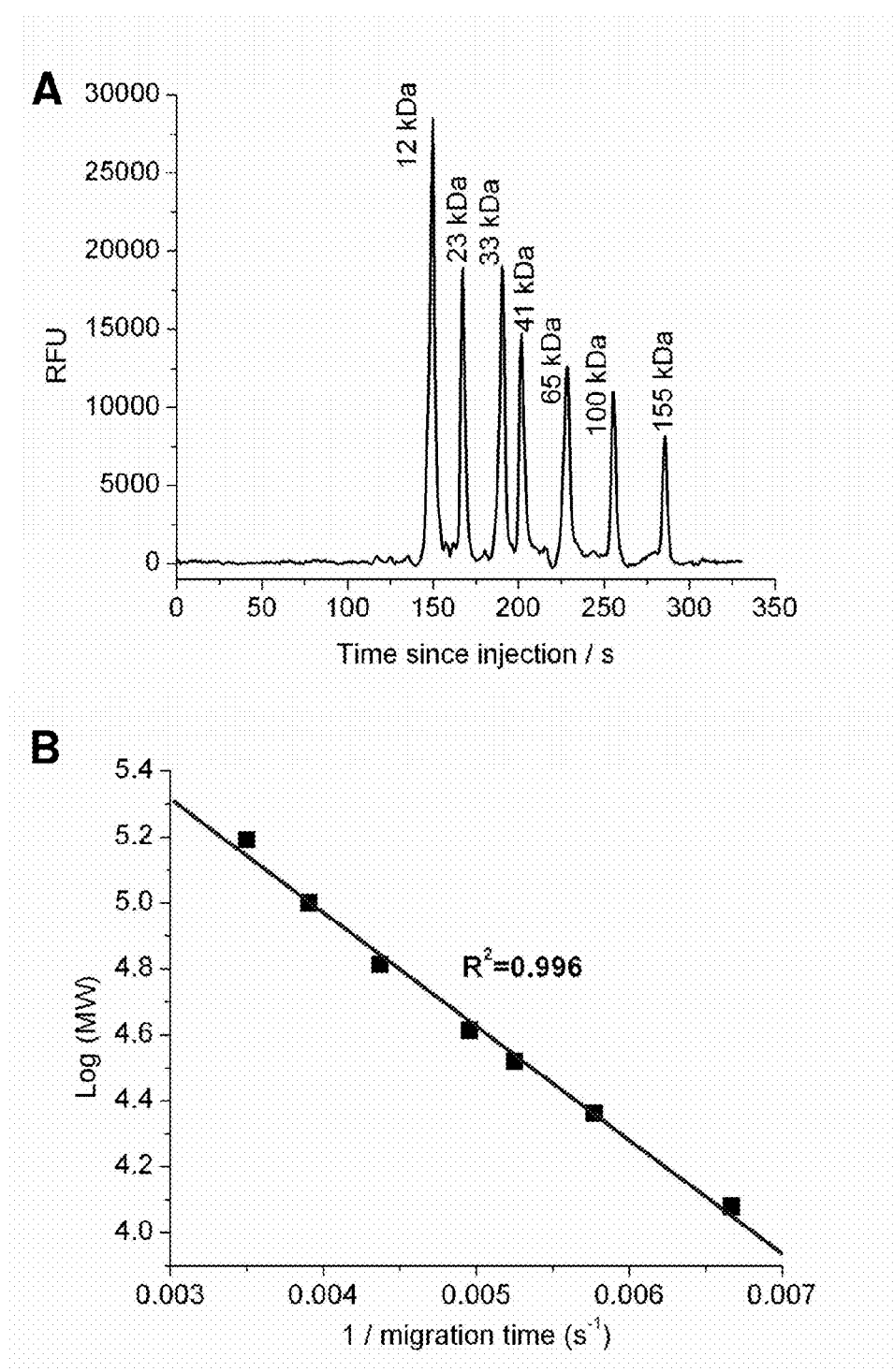

FIG. 13. Size-dependent separations of BenchMark™ Fluorescent Protein Standard performed using the microfluidic chip depicted in FIG. 12. (A) 7 proteins that make up the standard. The molecular weights for the labeled proteins are noted beside each observed peak. (B) Plotting log MW as a function of inverse migration time yields a linear plot for these Alexa Fluor® 488-labeled proteins.

Figure 14:
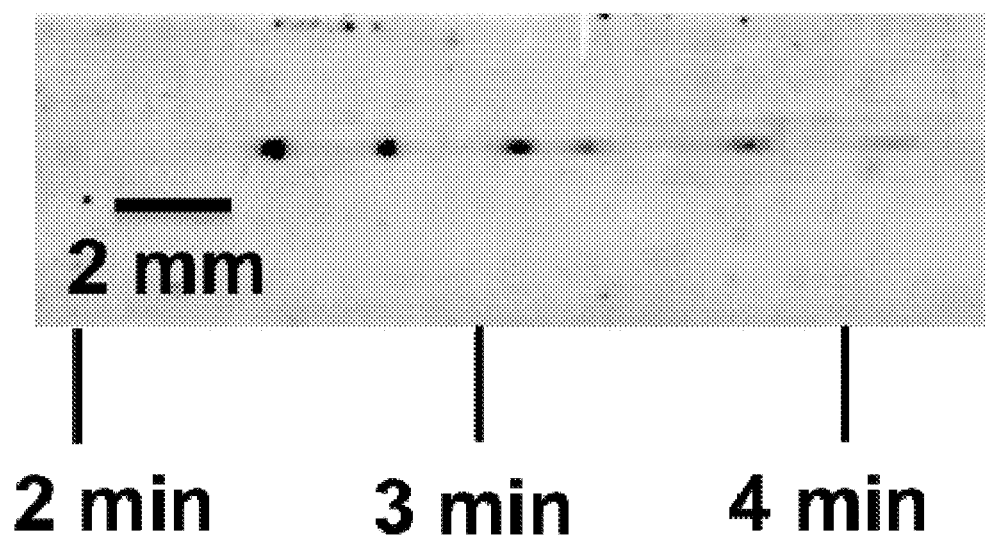

FIG. 14. Fluorescent scan of a size-dependent separation of a protein ladder deposited on a membrane. The membrane was moving at 6 mm/min. The separation electric field was 280 V/cm.

Figure 15:
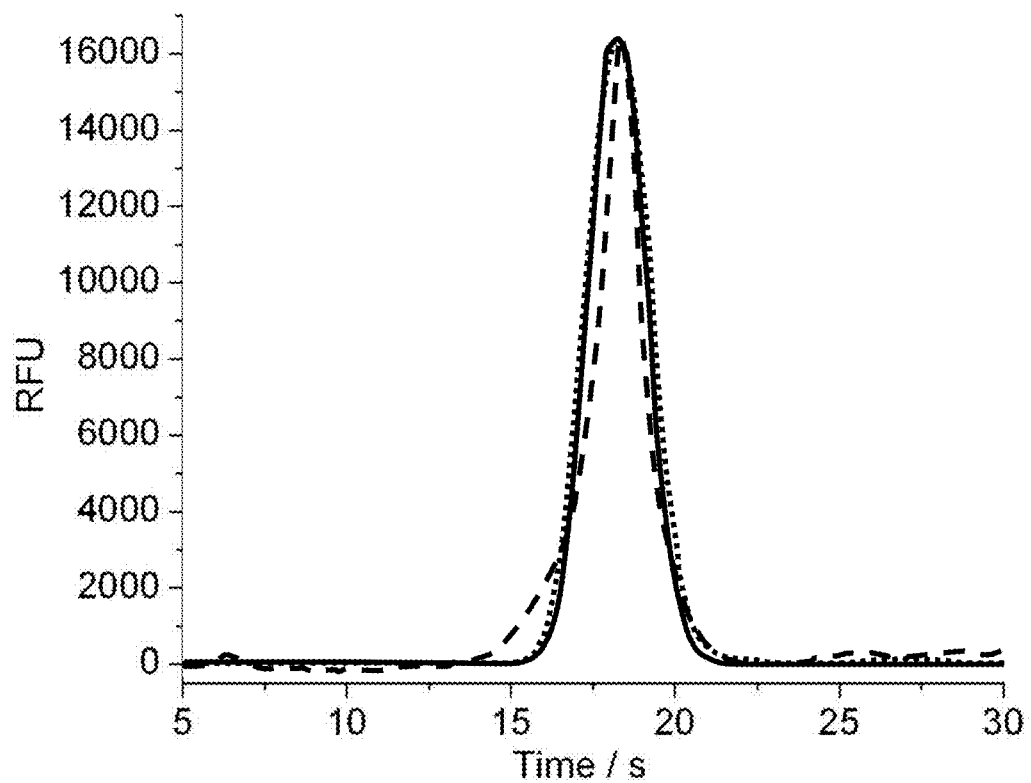

FIG. 15. Comparison of peak width in the electrophoresis channel (solid line), 300 µm in the post-column channel (dotted line), and on a membrane (dashed line). All the data were taken from the same separation. 0.5 mg/mL FITC-BSA was used as sample in this experiment.

Figure 16:
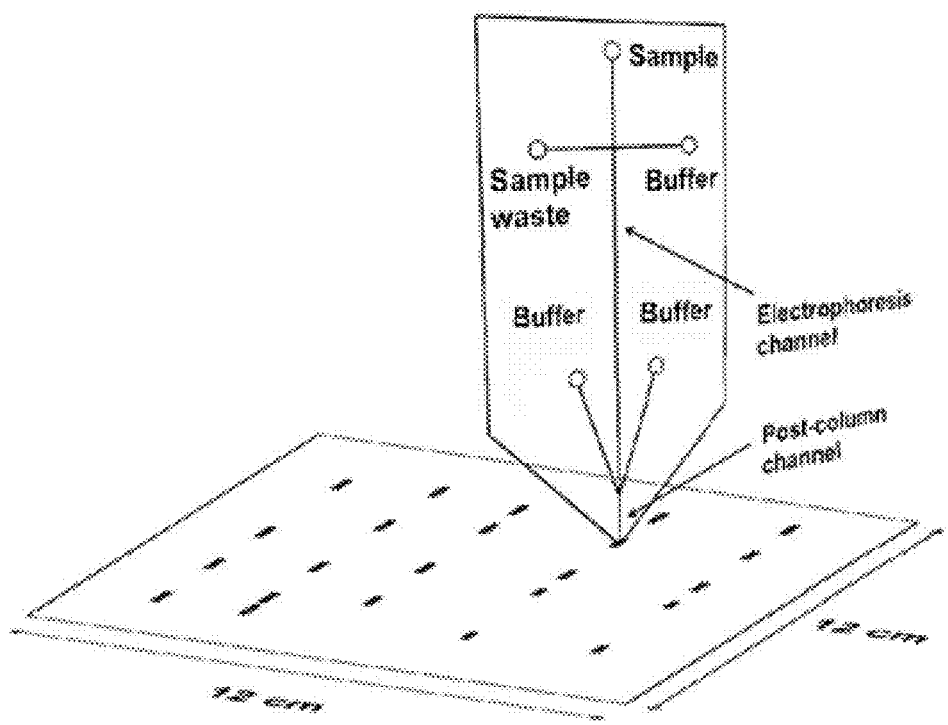

FIG. 16. 3D view of microfluidic chip-based high-throughput western blotting with multiple separation tracks on the same membrane. Multiple injections can be captured on a single membrane.

Figure 17:
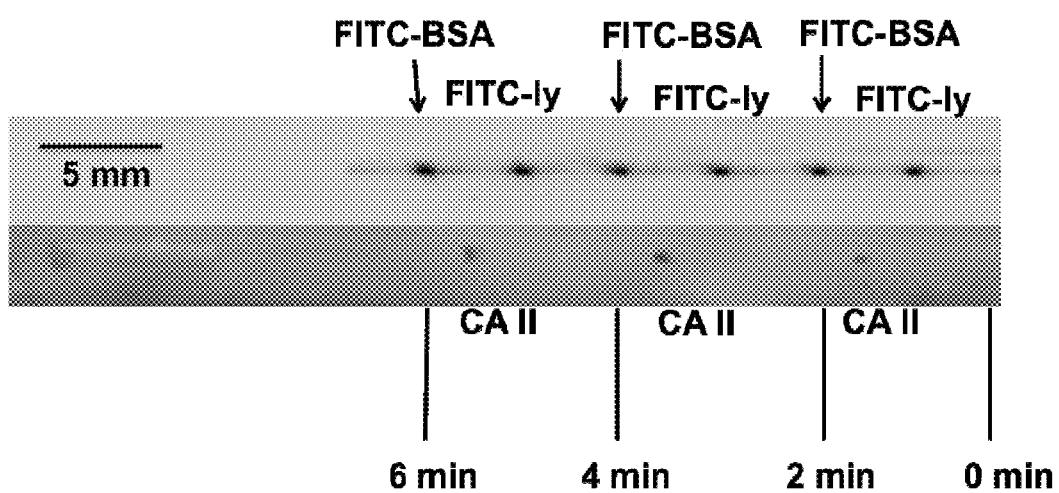

FIG. 17. Microfluidic chip-based separation of carbonic anhydrase II (CAII), FITC-BSA, and FITC-lysozyme. 3 injections were performed with 2 minute intervals between the injections. The electric field applied was 340 V/cm and the membrane was moving at 3.5 mm/min. The samples were deposited on a membrane in a single dimension. After the contents of the third injection eluted onto the moving membrane, the membrane was subjected to both a fluorescent scan, and a western blot with an anti-CAII primary antibody, and a Snap I.d.® Protein Detection System from Millipore. (A) Fluorescent scan. (B) Western blot.

Figure 18:
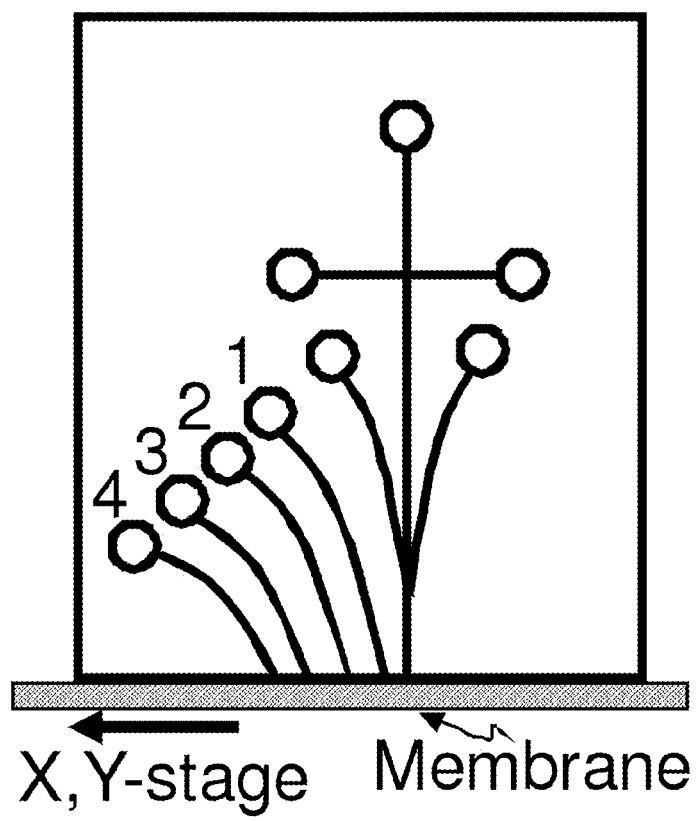

FIG. 18. Embodiment of a microfluidic chip based system for on-line addition of immunoassay reagents. Reservoirs (shown as circles) can include those shown in FIG. 11. For example, blocking agent, rinse, primary antibody, and secondary antibody can be added from reservoirs 1, 2, 3, and 4, respectively. Addition can be controlled by voltage or pressure.

DETAILED DESCRIPTION

The following description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom. A non-limiting discussion of terms and phrases intended to aid understanding of the present technology is provided at the end of this Detailed Description.

The present technology relates to electrophoresis and blotting systems that include a capillary or microfluidic channel. In some embodiments, a highly miniaturized Western blot is provided that uses capillary electrophoresis (CE) separation of SDS-protein complexes directly coupled to a PVDF immunoblotting membrane. This is achieved by dragging a gel-sheathed, gel-filled separation capillary along the surface of a blotting membrane. High voltage is applied to the capillary at the inlet, which is then electrically coupled through the wetted membrane to an XY-translational stage below. The membrane on the translational stage can be continuously moved past the stationary capillary (or vice versa where the capillary is moved past the stationary translational stage), collecting eluted proteins of increasing sizes onto the blotting membrane without a separate transfer step. The separation is thus preserved for analysis by immunological methods. The blotting membrane can be moistened with a methanol and buffer mixture to facilitate protein adsorption.

As an example, a Western blot for lysozyme can be completed in about one hour with about a 50 pg mass detection limit from low microgram per milliliter samples. Although discrete protein zones can be detected, bands may be broadened by about 1.7-fold upon transfer to the membrane. The present systems and methods provide a substantial reduction in time requirements and an improvement in mass sensitivity compared to conventional Western blots. Analysis of low volume samples can be accomplished with reduced reagents and time, while retaining the information content of a conventional Western blot.

A variety of affinity-CE techniques have been developed including immunoassays (Ding et al., *Electrophoresis* 2001, 22, 2210-2216; Kiessig et al., *Electrophoresis* 2001, 22, 1428-1435; O'Neill et al., *Proc. Natl. Acad. Sci. U.S.A.* 2006, 103, 16153-16158; Schou et al., *Electrophoresis* 2006, 27, 44-59; Roper et al., *Anal. Chem.* 2003, 75, 4711-4717). Capillary isoelectric focusing has been used to separate proteins which are then immobilized by photoactivated cross-linking to the capillary surface (O'Neill et al., *Proc. Natl. Acad. Sci. U.S.A.* 2006, 103, 16153-16158). The captured proteins are detected in the capillary by immunoassays performed by flushing antibodies and reagents through the capillary. The method provides excellent sensitivity and separation; but, the instrument used is expensive and the method does not provide the size-based separation of a classical Western blot.

Methods for capturing proteins separated by CE onto a membrane have also been described (Eriksson et al., *Anal. Biochem.* 1992, 201, 211-215; Zhang et al., *J. Mass Spectrom.* 1996, 31, 1039-1046; Yeung et al., *J. Chromatogr.*, A 2001, 931, 153-162; Johnson et al., *Anal. Chem.* 2001, 73, 1670-1675). The majority of these techniques are directed towards off-column mass spectrometry detection, although one did use antibody detection (Eriksson et al., *Anal. Biochem.* 1992, 201, 211-215). However, none of these methods for membrane capture of proteins separated by CE used size-based separations; therefore, they do not provide the platform needed for Western blotting. Size-based separation of proteins in capillary and chip-based gel electrophoresis formats has been demonstrated (Michels et al., *Anal. Chem.* 2007, 79, 5963-5971; Bousse et al., *Anal. Chem.* 2001, 73, 1207-1212). These studies show that smaller channel dimensions reduce sample volumes and enables higher electric fields (typically up to about 300 V/cm) relative to slab gels.

The present technology discloses a capillary gel electrophoresis (CGE)-Western blot. A gel-filled capillary is interfaced with a blotting membrane, which captures protein as it migrates from the capillary and eliminates the need for a separate electro-blotting step in comparison to slab gel Western blots. The use of CE separations in capillaries and microfluidic channels leads to better mass sensitivity as well as faster separation when compared to slab gel Western blots. CE also allows use of entangled polymer solutions instead of cross-linked gels. Entangled polymer solutions facilitate automation and reduce the time for gel preparation because capillaries can be emptied and refilled by pumping as necessary to maintain consistent separation performance. This is unlike cross-linked gels which must be formed within the capillary (Zhang et al., *Electrophoresis* 2006, 27, 3086-3092; Quigley et al., *Anal. Chem.* 2004, 76, 4645-4658). Faster separation, the elimination of an electro-blotting step, and recent improvement in commercial immunoassay instrumentation combine for a reduction in total Western blot analysis time to under two hours. Because the immunoassay can be performed in parallel and the separation step is relatively fast, higher throughput can be achieved by performing a series of separations that are captured on a single membrane for simultaneous immunoassay. Further, the use of a plurality of capillaries or channels allows for separations in parallel, and further increase the throughput. The techniques disclosed herein provide improved throughput, automation, and mass sensitivity while retaining the information content and ease of use of a traditional Western blot.

Materials and Reagents. Fluorescein isothiocyanate (FITC) and FITC-labeled insulin were purchased from Invitrogen (Carlsbad, Calif.). ECL Plus chemifluorescence kit and polyvinylidene fluoride (PVDF) membranes were purchased from GE Healthcare (Piscataway, N.J.) and GE Osmonics (Minnetonka, Minn.) respectively. Rabbit anti-lysozyme was purchased from Millipore (Bedford, Mass.) and rabbit anti-carbonic anhydrase from Genway Biotech (San Diego, Calif.). FITC-labeled bovine serum albumin (BSA), and the secondary antibody, horseradish peroxidase-conjugated anti-rabbit IgG produced in goat, were purchased from Sigma (St. Louis, Mo.). Other unlabeled proteins and all other chemicals were purchased from Sigma. Fused silica capillaries were from Polymicro (Phoenix, Ariz.). All solutions were made using Milli-Q (Millipore) 18 MΩ deionized water. Phosphate buffer solution (PBS) was 100 mM $Na_2HPO_4$ adjusted to pH 7.5 with 100 mM $NaH_2PO_4$. Electrophoresis buffer for free solution CE was 100 mM Tris adjusted to pH 8.8 with HCl. Sieving media was a proprietary solution of entangled polymers designed for resolution of proteins from 10 kDa to 225 kDa (part number 390953 from Beckman-Coulter, Brea, Calif.). This media had a kinematic viscosity of 78 cp at 40° C. as measured using a glass semi-micro viscometer (Cannon Instrument, State College, Pa., USA).

Sample Preparation. Proteins were denatured by heating at 70° C. for 5 min in denaturation buffer consisting of PBS, 3% sodium dodecyl sulfate (SDS) and 5% β-mercaptoethanol (BME). In some instances, protein samples were then dialyzed against PBS using mini-dialysis cups (Pierce Biotechnology, Rockford, Ill.). Protein samples for injection were diluted from these sample stocks with 25 mM Tris adjusted to pH 8.8 with HCl. In some experiments, proteins were first labeled with FITC, then denatured and dialysed. FITC prepared at 1 mg/mL in dimethyl sulfoxide was diluted to a final concentration of 100 µg/mL and incubated for 1 h with protein at 1-5 mg/mL in PBS for labeling.

Apparatus and Procedure for CE Western Blot. A diagram of the apparatus used to couple the separation capillary to the blotting membrane is shown in FIG. 1. High voltage was applied at the separation capillary inlet reservoir and grounded at the stage. The separation capillary outlet was surrounded by a gel-filled sheath capillary that made contact with a PVDF membrane secured to the X-Y translational stage. During injection and separation, the sheath capillary, fixed at an angle of approximately 45°, was positioned to make light contact with the membrane (determined by slowly lowering the capillary until it bent). The stage moved the blot past the capillary at a rate of 3 mm/min, which was the slowest setting possible for the motorized stage. A LabVIEW program controlled stage motion and application of high voltage. The maximum distance traveled by the stage, as constrained by the stepper motor track length, was 13 cm. Typically, a 0.5 cm by 12 cm blotting membrane was mounted on the stage, though a separation may require a shorter length. The footprint of the apparatus, including the stage, stepper motors, and capillary positioner is about 40 cm by 40 cm.

Polyimide-coated fused silica capillaries were used for both the separation and sheath capillaries. The separation capillary (20 cm in length, 50 µm ID, 185 µm OD) was threaded through a sheath capillary (6.5 cm long, 250 µm ID, 360 µm OD) and fixed in place using a PEEK tee (VICI Valco Instruments, Houston, Tex.). The sheath capillary extended past the separation capillary by 0.5 mm. During separations electrophoresis gel was pumped through the sheath capillary at 10 mL/min using a syringe pump (Fusion 400, Chemyx, Stafford, Tex.). Separation capillaries were conditioned by sequential rinsing with 0.1 M NaOH, 0.1 M HCl, and water for 10, 5, and 2 min respectively, followed by pumping gel through the capillary (10 min) as recommended by the manufacturer. Gel-filled capillaries were used for 3 to 5 injections before regeneration with further conditioning.

The PVDF membrane mounted on the stage was kept wet with a wick that overlaid the membrane prior to contact with the capillary. The wick was kept stationary so that the membrane on the stage moved out from under it just before contact with the capillary. Both the membrane and wick were wetted with 50:50 (v:v) methanol and electrophoresis buffer. After a region of membrane passed the capillary it was allowed to dry.

Detection on Membrane. Fluorescent proteins were detected on the membrane by direct imaging using a Typhoon 9410 variable mode imager (GE Healthcare) in fluorescence mode. For Western blot analyses, immunoassays were performed per instructions of the manufacturer using a SNAP i.d. unit (Millipore), which partially automates antibody incubation and wash steps. In this system, 10 mL of blocking solution, 1 mL volume of antibody solutions, and tens of mL of rinse buffer, are poured over the surface of the blot (28 cm² in area in this case) in the normal sequence. After incubation (10 min for each antibody step) solution is forced through the PVDF membrane using a vacuum pump. Design of the unit, including a cartridge which holds the blot stationary, prevents membrane drying. The primary antibody sera to each target protein were diluted to 1:1700 and the secondary antibody was diluted to 1:33000. All dilutions were made with electrophoresis buffer. 0.5% nonfat dry milk and 0.5% Tween 20 were used in the blocking and rinse steps, respectively, per manufacturer suggestions. Signal generation, using hydrogen peroxide and acridan ester substrates in a chemifluorescence kit (ECL Plus, GE Healthcare), was catalyzed by horseradish peroxidase-conjugated secondary antibody.

Capillary Gel Electrophoresis (CGE). For comparison to the X-Y translational stage apparatus, experiments were conducted using a P/ACE MDQ capillary electrophoresis unit equipped with an LIF detector (Beckman-Coulter, Fullerton, Calif., USA). The detector used 5 mW of 488 nm light from an $Ar^+$ laser (Model: IMA101015B0S; Melles Griot, Carlsbad, Calif., USA) for excitation. Emission was detected after passing through a 488 nm notch filter and a 520±10 nm band-pass filter. Capillaries had an effective length of 20 cm, 50 µm ID, and 360 µm OD. Separation capillaries were treated as described above for the membrane capture experiments. Fluorescence imaging of proteins migrating from separation capillary outlet into the sheath capillary region was performed using an inverted epi-fluorescence microscope (IX71, OlympusAmerica, Inc., Melville, N.Y.) and CCD camera (C9100-13, Hamamatsu Photonic Systems, Bridgewater, N.J.) as described in detail by Dishinger et al., *Anal. Chem.* 2009, 81 (8), 3119-3127. In these experiments the capillaries were of similar dimensions to those of the CE-Western blot, except that the sheath capillary extended 5 cm beyond the separation capillary and was grounded in a gel reservoir rather than to a moving surface.

These experiments produced the following results.

SDS-protein complex capture from CGE. Our approach to CE-based Western blot was to capture SDS-protein complexes onto a membrane as they migrated from the column using the system shown in FIG. 1 and then detect them using conventional immunoassay. Initial experiments were directed at identifying conditions that would allow protein capture with minimal band spreading using fluorescently-labeled proteins as a model. FIG. 2 illustrates images from the direct detection on a PVDF membrane of captured FITC-labeled proteins that had been separated by CGE as SDS-complexes. PVDF membrane was chosen as the blotting membrane because of its reported high binding capacity and mechanical strength; however, this method could also be used with different substrates. For example, nitrocellulose did allow for electrophoresis, though the membrane was brittle and difficult to manipulate (data not shown). With this work utilizing PVDF membranes, proteins are captured in discrete zones, preserving the separation. Furthermore, proteins migrated according to log molecular weight as expected for CGE of SDS-complexes (FIG. 2).

Reproducibility of migration time (measured as distance on the membrane) was good with FITC-labeled BSA and insulin peaks observed at 34.3±0.8 min and 18.8±0.6 min respectively (n=3). These samples separated on a commercial CE-LIF instrument with the same nominal conditions (capillary length, i.d., buffer, and electric field) had longer migration times at 41.5±1.5 min and 23.14±0.02 min (n=3) respectively. A likely cause of this difference was a lack of provision for cooling on the blotting instrument, compared to active cooling to 22-24° C. on the commercial apparatus. Supporting this conclusion, we found that separations performed without temperature control (ambient temperature was about 26° C.) and with on-column detection yielded migration times (29.9±0.2 and 16.5±0.1 min (n=3) for BSA and insulin respectively) that were more similar to those obtained by membrane capture.

Although capturing native proteins on surfaces after separation by free solution CE has been demonstrated, we found that several modifications are necessary to capture proteins separated as SDS complexes by CGE and achieve detection of discrete bands, as shown in FIG. 2. In particular, it is preferable to wet the capture membrane with a solution such as a methanol:electrophoresis transfer buffer (a 50:50 v:v mixture was used). Without the transfer buffer (i.e. methanol) present during capture, either no bands or diminished signal was observed. Methanol helps to wet the PVDF membrane and to dissociate the SDS-protein complex which improves adsorption onto the hydrophobic membrane. A wick overlaid the membrane prior to capture, and helped to prevent evaporation of the transfer buffer during CGE separation. The effect of the transfer buffer is illustrated in FIG. 7.

A second modification includes use of a gel-filled sheath capillary around the outside of the separation capillary (FIGS. 1 and 8). Without a sheath capillary, electrophoresis current was unstable and bubble formation was observed in the separation capillary a few minutes after voltage was applied (FIG. 8). If gel in the sheath was static, i.e. without flow, migration times were irregular and the current was only stable for about 15 min before drift occurred. Pumping the sheath fluid at 10 mL/min alleviated these problems. Higher sheath gel flow rates (50-200 mL/min) were found to smear protein on the blot. The underlying cause of these effects was not investigated, but they are consistent with electrolysis induced alterations in electrolyte at the outlet. Specifically, it has been observed that when the outlet vial has a small volume, such as the thin layer of buffer on the blotting membrane, $OH^-$ formed at the outlet may migrate towards the inlet to cause changes in pH and conductivity in the capillary. The sheath capillary will dilute $OH^-$ formed and create a low field region that slows the $OH^-$ migration towards the inlet. With a supplemental flow, the $OH^-$ may be prevented from entering the separation capillary at all. The sheath flow capillary also prevents a sharp electric field boundary along with buffer change at the outlet of the separation capillary which may also contribute to the stability observed.

Band broadening. Although proteins are detected in discrete bands, we found that the system produced bands that were approximately 1.7 fold broader than on-column detection. To determine the source of band broadening, zones detected on membrane were compared to those detected on-column and within the sheath-flow capillary. For these experiments, the membrane capture experiment was performed as before (e.g., FIG. 2A). A separate measurement was done to detect on-column and in the sheath simultaneously using an imaging system under similar separation conditions (i.e., sample composition, column length, column i.d., buffer, and electric field). Separate experiments were required because of the impracticality of detecting on-capillary while also capturing zones on a membrane. For both measurements, FITC-BSA was used as a test compound. Peak variance for FITC-BSA increased from 230 $s^2$ on capillary to 610 $s^2$ in the sheath (350 μm downstream of the separation capillary) to 670 $s^2$ on the membrane (see FIG. 3A). These results indicate that the majority of band broadening in transfer from the capillary to membrane occurs within the sheath itself. Images of the transfer from capillary to sheath (FIG. 3B) provide insight into some of the reasons for this band broadening. The parabolic flow induced in the sheath, evident from the bullet shaped zone, adds band broadening. (Recall that flow was important to maintain stable currents). The decreased electric field in the sheath capillary, due to the wider bore and lower electrical resistance compared the separation capillary, may also contribute to the band broadening. These results indicate that fabrication of a sheath with narrower bore, perhaps through microfabrication methods, may decrease band broadening and improve resolution. The imaging results also show that the zone is not focused by the sheath flow, as is observed with higher flow rates. The post-separation band broadening effect can be substantially reduced by using the embodiment shown in FIG. 11 as illustrated by the results shown in FIG. 15.

When SDS-protein complexes migrate onto the membrane, most of the spreading on the blot appears to be laterally across the surface, rather than down into the membrane. Evaluation of spreading in the dimension perpendicular to the motion of the capillary indicates a typical trace width of approximately 450 μm, about 200 μm larger than the width of the sheath capillary inner diameter (FIG. 4). Yet in the vertical dimension protein was not detected beyond the first 150 μm thick membrane when deposition was performed onto a stack of membranes. This result is in contrast to previous work that indicated some protein penetrated a first membrane and bound the second (Eriksson et al., *Anal. Biochem.* 1992, 201, 211-215). In that work, 20 ng of protein was deposited whereas in this work picograms of proteins were deposited, so it could be that the spread through the membrane is too low for detection via immunoassay. These results support the idea of rapid protein capture.

Improvements in separation efficiency may be possible with this method. Provision for cooling or use of narrower-bore capillaries would minimize heating effects in the gel. This effect is illustrated in FIG. 13 where narrow channels were used as the separation conduit. Fabrication of lower volume sheath capillaries or channels (e.g., FIG. 11) may also avoid extra-column broadening (illustrated in FIG. 15). Finally, some improvement may be obtained in membrane capture. Focusing the electric field near the capillary outlet or using vacuum deposition following a liquid junction can ameliorate spreading during deposition with free solution CE; however, the interfaces previously used with free solution CE are unlikely to be compatible with gel-based separations because of the lack of electroosmotic flow and sensitivity to the outlet buffer composition for CGE.

Immunoblotting after capillary separation. FIG. 4 illustrates a CGE-Western blot for lysozyme at different concentrations. As with traditional slab-gel Western blots, this technique is semi-quantitative allowing for differences in protein concentration to be determined by the intensity of the band detected, as shown in FIG. 4. An advantage of the CE method over traditional Western blots is elimination of a separate electro-blotting step because protein is directly delivered to the membrane as it is separated. This saves time as transfer requires up to 1 h in a conventional slab gel system. In this system, a smaller protein like lysozyme (MW=14.3 kDa) migrated onto the membrane in about 15 min. Combined with the 30 min semi-automated commercial immunoassay platform and 10 min for incubation in detection reagents and fluorescence scanning, these Western blots were completed in less than 1 h, excluding sample preparation. Larger proteins, such as BSA, would extend total time to about 1.5 h.

Limits of detection (LOD). The limit of detection was investigated by performing CGE-Western blot of carbonic anhydrase and lysozyme at concentrations that produced weak signals (FIG. 5). In these experiments, sample concentrations of 25 and 20 μg/mL resulted in peaks with signal-to-noise ratio (S/N) of 22 and 12 for carbonic anhydrase and lysozyme respectively. Assuming a linear response, this S/N corresponds to a LOD of 3 μg/mL or 10 pg injected for carbonic anhydrase and 5 μg/mL or 50 pg injected for lysozyme. (Amounts injected were estimated using injection duration, sample concentration and sample mobility.) The manufacturer reports the LOD for the chemifluorescence assay kit to be low picograms, so the sensitivity of our scheme is on par with the capabilities of the detection method. The good mass LOD for this system is attributed to use of small bore capillaries and small capture zones. Further, recovery may be higher in CGE because proteins are migrated from a low-volume sieving polymer matrix rather than electro-transferred out of a cross-linked slab gel for blotting.

The rate of stage motion past the capillary may also impact LOD and resolution. Lower speeds are preferable to capture the band in a small zone and improve sensitivity by keeping the zone concentrated; however, if the speed is too low, zones would be captured with little distance between them, and resolution may be lost. In our experiments we used the lowest speed of the translational stage because no resolution was lost when compared to higher speeds, but the zones were more concentrated on the membrane. A stage with slower translational velocity therefore may allow better sensitivity.

Incorporation of size standards. An important component of a Western blot is providing size information on the detected proteins in addition to immunoaffinity. The size of the target protein is estimated by comparison of its mobility to the mobility of a different proteins of known size separated in an adjacent lane. One approach for calibration in the CGE system is to add fluorescently-labeled protein size standards to the sample mixture and analyze the membrane by both direct fluorescence and immunoblotting. Results from such an experiment are illustrated in FIG. 6. In the initial fluorescence scan, the added calibrants, FITC-insulin and FITC-BSA, are detected to provide reference positions on the membrane. The membrane is then probed with antibodies specific for the analyte protein, carbonic anhydrase. The signal for this protein is detected as a band between the reference bands, as anticipated because of its intermediate molecular weight. During the second analysis of the membrane, the standard proteins are barely detectable. This may be because the chemifluorescent signal from the secondary antibody conjugate is more intense than the fluorescent ladder proteins. The signal of the ladder proteins may also be reduced by photobleaching or rinsing prior to the second detection step.

These experiments validate performing CE-based Western blots. The system allows separation and blotting to occur at the same time thus eliminating the time for electro-blotting. Although the described approach demonstrates the capacity for reducing sample requirements, automating, and reducing time of Western blots, further improvements in time of analysis, robustness, throughput, and LOD are also possible. For example, the system can include active cooling of the separation capillary, use of a smaller i.d., or a different sieving matrix to tune the system for faster and/or higher efficiency separations. As indicated by microfluidic gel sieving, extremely fast protein size separations are possible in miniaturized formats, where the separation and blotting time may be reduced to less than 1 min. Throughput can also be improved by use of multiple capillaries in parallel. Parallelization also allows molecular weight markers or ladder proteins to be run in a separate capillary for sizing if desired. A further throughput improvement includes automating gel-regeneration, as has been done for DNA sequencing instruments. Entangled polymer gel may also be used as it can be more amenable to transfer of large proteins. On-column sample pre-concentration is also possible in CGE, and can further improve concentration LODs. The translational stage velocity can be tuned to improve either resolution or sensitivity. Finally, the small size of the capillary and resulting tracks make it possible to store many electropherograms on a small membrane to reduce reagent consumption and improve throughput relative to a traditional slab-gel Western blot.

CE is recognized as a powerful method for protein separations; however, it can be argued that widespread acceptance of CE for protein analysis has been inhibited by lack of an analog to Western blotting. The present technology demonstrates CE-Western blotting. Many improvements result from the migration from a slab-gel to the capillary format, as demonstrated herein. The time of analysis is improved through faster separation, use of polymer solutions for sieving media, and elimination of the electro-blotting step. Mass detection limits of 10 pg can be readily achieved with little optimization. The present systems and methods provide for substantial improvements in speed, throughput, reagent consumption, and sensitivity. Importantly, the systems and methods also retain the essential features of the traditional Western blot format by providing size (calibrated with standards) and immunoaffinity information in a semi-quantitative assay. Furthermore, method development is the same as a Western blot so that detection and development of assays for different proteins follows well-established procedures including commercially available protocols. This is exemplified by the fact that we were able to readily develop Western blots for 3 different proteins in the course of this work. The present technology is particularly advantageous for sample-limited analyses or in situations where better speed, throughput or automation is necessary.

The following variations relating to electrophoresis and blotting systems, apparatus, and methods are part of the present technology. In a CE method, a sieving separation can be performed in a capillary and the output collected onto a blotting membrane for detection by antibody. This method can provide better mass sensitivity (e.g., fmol or better LODs), higher throughput (e.g., over 20-fold improvement), reduction of reagents, improved portability, and can be automated, as compared to traditional Western blot methods.

There are various ways to tailor aspects of the systems and methods provided herein. The first is that the PVDF membrane can be wetted with a methanolic solution. A 50:50 methanol:aqueous transfer buffer can be used, although other organic solvents and different compositions may also be used. FIG. 7 illustrates improved capture of protein on a PVDF membrane that is coated with methanol compared to fully aqueous solution. In addition, the PVDF membrane can be kept wet with transfer buffer during the separation. This can be achieved by placing a wick that dragged over the membrane just ahead of the capillary, as shown in FIG. 1. To improve operation of the system, it can also be beneficial to have the sheath capillary provide a gel solution around the outlet of the capillary. FIG. 8 shows a close up picture of the sheath capillary. In some cases, without this addition the separations could not reliably be performed. Other systems of providing gel at the outside of the capillary may also be utilized, such as a side-by-side capillary or using a gel impregnated membrane.

Membranes used in the present technology can include the following aspects. Protein capture on membranes from capillaries should be highly efficient thus preserving the quality of the separation. PVDF membranes have been found to produce results that suggest good capture efficiency following electrophoretic separation; however, other membranes can be used. For example, other commercially available membranes with excellent protein binding properties, such as nitrocellulose and nylon, may be used. In addition to membrane composition, membrane thickness and porosity can be modified. Thinner membranes (e.g., commercially available down to 10 μm thick) can blot faster, can have sufficient capacity for small samples, can give better sensitivity, and can improve reproducibility, as demonstrated for dot-blot methods. Besides such traditional blotting membranes, an alternative membrane includes HP Plotter paper. This membranous material, which is designed to capture dye molecules with high resolution, is remarkably effective at trapping peptides from CE-separations. Additionally, covalent capture of proteins onto epoxide coated plates (e.g., ArrayIt, www.arrayit.com), which are presently used for creating protein arrays, can be used in place of the traditional membrane. If substantial band broadening from the adsorption step occurs, use of dried membranes or membranes under vacuum, which have previously been shown to aid preservation of efficiency, may be used.

Size-standards can be employed in the present technology. When separating proteins by sieving (e.g., sodium dodecyl sulfate polyacrylamide gel electrophoresis (SDS-PAGE)), it can be advantageous to also separate a series of standards that vary in molecular weight. Standards can include a series of several proteins that span a molecular weight range (e.g., 14.4 to 200 kDA, such as BioRad size ladder) that have been labeled with 5-furoylquinoline-3-carboxaldehyde (FQ) or Alexa Fluor 488 or other fluorophore. These labels have been found to be compatible with capillary SDS-PAGE.

For the capillary electrophoresis (CE) Western, standards can be mixed in with the sample and separated at the same time. If fluorescence is used for detection of the analyte proteins, then different color fluorophores can be used for the standards and the secondary antibody. For example, the standards can be labeled with FQ and the secondary antibody with rhodamine. If the secondary antibody is labeled with a chemiluminescent label, then separate detectors could be used. Another option is to perform separate electrophoretic analyses for standards and sample so that the sizing standards are laid on the membrane in a track parallel to the sample. The separate analysis could be performed by having two identical capillaries operated in parallel or operating one capillary twice, once for standards and once for sample. The best option may depend on which approach offers the best reproducibility and measurement of analytes versus standards with respect to any signal overlap, for example. One advantage of the parallel approach is that a single detection system could be used.

Although fluorescent proteins can be used as standards, it should be recognized that the labeling procedure may alter the properties of the proteins including their ability to bind to membranes. Therefore, unlabeled proteins can be used along with UV-absorbance detection (on-line) and Ag-staining (off-line). For example, these approaches can be used where the membrane chosen has background fluorescence.

The present technology allows for parallel operation. An advantage of traditional Western blots in slab gels is the ease with which multiple samples can be analyzed in parallel on a single gel. A similar parallelization of capillaries is possible with the present technology. For the membrane fraction collection method, this requires using a bundle of capillaries that can be operated simultaneously with the same power supply. For example, the capillary system can be adapted to use several (e.g., 16) capillaries that are positioned at the membrane together. Alternatively, a microfluidic chip comprising multiple channels can be used to increase throughput of the system.

Simultaneous addition of reagents and separation can be performed using the present methods and systems. Although the separation and protein transfer step of the Western blot are miniaturized and faster with the present approach, the subsequent immunoassay step, which involves blocking the membrane with protein and then adding antibody against the target protein is not necessarily any faster that traditional Western blotting methods. However, a variation that is possible with the present capillary system is to simultaneously and continuously add the blocking and antibody solutions through extra capillaries mounted on the XY-stage along with the separation capillary, as illustrated in FIG. 9. By pumping solution through these capillaries (e.g., by syringe pump, gas pressure, or electroosmosis) the blotting and antibody binding step can be performed as the protein is being blotted, therefore reducing the overall analysis time.

The present technology further relates to microfluidic electrophoresis and blotting systems based on electrophoretic separation of a sample (e.g., sodium dodecyl sulfate protein complexes) using a microfluidic channel followed by electroblotting and deposition onto a blotting membrane for immunoassay. In a microfluidic system, the separation can be performed in a channel that is bounded by a porous membrane (e.g., a nanoporous membrane). After separation, the proteins can be electrotransferred through the porous membrane to a blotting membrane which is then assayed with an antibody.

The microfluidic system can be a chip-based system. In this approach, samples are not migrated entirely through the capillary or channel. Rather, like a conventional slab gel, the proteins electrophorese for a fixed period and are then transferred from the gel to the blotting membrane. To achieve this, the separation can be performed within a channel bounded by a porous membrane (FIG. 10 A, B). In this chip, a sample of analyte(s) (e.g., SDS-protein complexes) is loaded into the sample reservoir (FIG. 10B). Injection and separation along the electrophoresis channel (filled with polyacrylamide or other sieving media) can be controlled by voltages V3, V4, V5, and V6 using gated injection. During this step, the buffer chamber above the capillary electrophoresis (CE) channel can be filled with electrophoresis buffer and the bottom layer can be resting on a wetted membrane or filter paper to keep the gel from drying through the porous membrane. After separation (e.g., less than about 1 min), the chip can be placed onto a blotting membrane and protein electrotransferred from the channel to the membrane by application of negative voltage at V1 and ground at V2 (FIG. 10A). Thin channels allow rapid transfer of proteins compared to a traditional gel. After transfer, protein can be detected on the blotting membrane as described for the capillary systems.

The microfluidic approach offers an advantage over the capillary system in that it does not require a moving stage or careful alignment of the exits with the membrane surface. By eliminating these parts, the microfluidic system can be more rugged, cheaper, and easier to operate. An easily portable system can be constructed that comprises a power supply, disposable chip(s), blotting membrane, and a luminometer for detection, for example. Such a system allows a technician to perform Western blots on site for applications in clinical, agricultural, or resource poor settings. The system can be operated in parallel with multiple channels on one chip or multiple chips placed on one or more membranes.

Fabrication and testing of a chip for use in the microfluidic system includes the following aspects. The chip can be fabricated using multi-layer, adhesive contact printing. This fabrication system can be designed to incorporate polycarbonate membranes between plastic (e.g., polymethylmethacrylate (PMMA) layers) to allow electrotransfer between fluidic layers on a chip. This process can be used for multiple layers (e.g., 11 layers). An embodiment used in the present system can have 4 layers (see FIG. 10C), which is within the bounds of such chip fabrication technology.

A piece of polycarbonate is machined to have a large well and several smaller through holes (e.g., 1 mm diameter), as illustrated in FIG. 10. This piece is stamped in epoxy and then pressed onto a nanoporous polycarbonate membrane (second from left in FIG. 10C). The electrophoresis and injection channels are fabricated in PMMA using an Al mask and reactive ion etching to produce a thin (10-50 μm) PMMA layer with the electrophoresis channel (depicted in Figure C). This layer is adhered to a glass carrier plate, contact printed with adhesive and attached to the polycarbonate layer above. After curing the adhesive, the glass carrier plate is removed by brief exposure to water at 50° C. Finally, the bottom membrane layer (far right in FIG. 10C) is attached to the underside of the electrophoresis channel through another adhesive contact printing step, resulting in the final product.

As with the capillary system, fluorescent proteins can be used with the microfluidic chip system. Samples are injected and separated to determine protein migration rates on the chip and to determine how long the voltage should be applied for the desired separation. Protein is then transferred to the membrane. Detection can be accomplished by blotting using procedures developed with the capillary system. The methods and systems can include single channel systems, parallel assays performed with multiple channels on one chip, and the use of multiple chips at the same time. Channels of about 10-50 µm in depth, about 10-100 µm in width, and about 5 to 10 mm in length can be used. The dimensions and electric field parameters can be tailored to provide the desired separation on the chip for various analytes.

Filling the channels on the chip with sieving media can include the following aspects. Care should be taken when pumping the relatively viscous sieving media (e.g., polyacrylamide) into the channels bounded by the membrane to prevent mechanical failure or delamination of the membrane/PMMA stack. For example, such membrane/stacks can be safely subjected to about 6 atm of pressure when loading the channels, which is more than is required for rapid filling of the channels with typical polyacrylamide media. However, should an issue arise, depending on the type of sieving media or the concentration of the sieving media, larger bore channels can be fabricated in order to lower the pressure required to load the channels.

Another issue relating to the microfluidic chip is keeping protein from diffusing through the porous membrane during separation where the protein is then outside of the channel and lost. Such leakage is typically not a problem where the separation is expected to last <1 min; however, if it becomes a problem, a focusing voltage can be applied from V1 and V2 (see FIG. 10A, B) during the separation. Application of negative voltages to both sides of the membrane serves to focus the analytes towards the vertical center of the electrophoresis channel and prevents this effect. What is more, the porous membrane can be a nanoporous membrane to minimize the opportunity for any material or liquid to diffuse or permeate through the porous membrane.

Protein transfer can be readily accomplished through the porous membrane (e.g., polycarbonate membrane). Pores of the porous membrane can be up to 400 nm, for example, which is large enough for transfer of most proteins. In addition, porous membranes such as polycarbonate membranes can be coated with hydrophilic polyvinylpyrrolidone which is not prone to protein adsorption. This hydrophilic coating or other such hydrophilic coatings further facilitates filling the channels with aqueous solutions, including the sieving media. Other porous membranes, such as alumina, can be used.

The present technology further relates to microfluidic electrophoresis and blotting systems based on electrophoretic separation of a sample (e.g., sodium dodecyl sulfate protein complexes) using a microfluidic channel where the sample can be electrophoresed out of the channel to a blotting surface that can include a blotting membrane. The outlet of the microfluidic channel and blotting surface can be moved relative to each other to translate the electrophoretic separation of sample to the blotting membrane. Such microfluidic systems couple electrophoresis with blotting and can further include concomitant detection methods, such as an immunoassay.

For example, a microfluidic system can be used to separate proteins by sodium dodecyl sulfate-polyacrylamide gel electrophoresis (SDS-PAGE) using a microfluidic channel where the proteins are blotted directly from the channel onto a moving membrane. To promote capture of protein on the hydrophobic membrane, another microfluidic channel can dispense a solution to promote stable electrical current with the moving membrane and another channel or the solution can further add a component that promotes rapid adsorption of protein. Using this system, separation times of less than 60 s and picogram detection limits can be achieved. Further embodiments can include a series of separate microfluidic channels to add one or more detection reagents (e.g., immunoassay reagents) as the electrophoretic separation and blotting are occurring in order to reduce total analysis time (e.g., to a few minutes) and can further include the use of parallel sample microfluidic channels or parallel series of microfluidic sample and detection channels to improve throughput.

The combination of electrophoresis and blotting by the present microfluidic systems can reduce sample band broadening on the blotting membrane. Band broadening can occur when a sample is diluted and/or the electric field character changes during blotting. Reduction of band broadening can improve various aspects of sample analysis including resolution, protein identification (e.g., by allowing more accurate molecular weight determination), and sensitivity (e.g., by creating more concentrated zones on the membrane).

In particular, low sample transfer efficiency issues that can manifest in combined electrophoretic separation and blotting may arise from band broadening associated with transfer from the sieving medium (within an electrophoresis capillary or microfluidic channel, for example) to the blotting component. Taking, for example, the embodiment of the capillary electrophoresis and blotting system as shown in FIG. 1, once a sample band exits the separation capillary, it may expand and dilute within the electrophoresis buffer or gel flowing through the sheath capillary. Further, the electrophoretic transfer rate may slow down at this point. Dilution and reduced velocity within this zone can be due to diffusion, a weaker electric field, and/or spreading of electric field lines in the larger bore sheath capillary.

To address these aspects, the microfluidic electrophoresis and blotting system can be fabricated from a chip that includes an electrophoresis channel in combination with a post-column channel (i.e., a post-sieving microfluidic channel) that can add electrophoresis buffer or gel, as shown in FIG. 11. The post-column channel can be inline with the electrophoresis microfluidic channel and positioned after a given length of the electrophoresis microfluidic channel so that it is coupled to the electrophoretically-resolved sample eluate. In this case, sample (e.g., protein) is transferred from the edge of the chip to a blotting membrane. This approach allows the post-electrophoresis channel to be reproducibly made of various length, width, and depth dimensions allowing optimization and precision in performance. For example, the post-column transfer channel can be fabricated to have a width and depth similar to the electrophoresis channel thereby avoiding electric field and dilution effects in blotting of the sample. This arrangement can therefore reduce or eliminate band broadening that can be observed when using the coaxial capillary system shown in FIGS. 1 and 8. Non-limiting dimensions for the electrophoresis and post-column microfluidic channels include about 13 µm deep by about 36 µm wide channels, where the electrophoresis channel can be about 1 cm in length. For example, FIG. 12 is a photograph of a microfluidic chip that was used experimentally. Excluding the post-column channel, all the channels were 15 μm deep and 50 μm wide. The post-column channel was 15 μm deep and 90 μm long. The electrophoresis channel was 2 cm long and the post-column channel was 3 mm long. The virtual elimination of band broadening is seen in FIG. 15.

Examples of electrophoresis and blotting using the microfluidic system can include the following aspects. To test a microfluidic chip, fluorescently-labeled proteins (e.g., an AlexaFluor 488 labeled-ladder from Invitrogen or an FITC-labeled ladder from Sigma) can be electrophoretically resolved and transferred to a membrane. The electrophoresis microfluidic channel can be filled with polyacrylamide gel solution (e.g., from Caliper or Beckman) and "pinched injections" performed, as described by Bousse L, et al. (2001) Protein sizing on a microchip. *Analytical Chemistry* 73 (6): 1207-1212. Separations can be performed at 200-350 V/cm. During separation, electrophoresis buffer or gel can be present or pumped through the post-column addition channel as the chip is moved or dragged along a blotting membrane wetted with a methanol-buffer mixture. Alternatively, the chip can be stationary and the blotting membrane can be translated past the post-column channel outlet. For example, FIG. 13 shows a separation of Invitrogen's BenchMark™ Fluorescent Protein Standard (protein standards conjugated to Alexa Fluor® 488), by use of the chip shown in FIG. 12. The total concentration of the protein ladder was about 1 mg/mL, and the separation electric field was 280 V/cm. Fluorescence was detected at the end of the electrophoresis channel, just upstream of the post-column channel. The raw data in FIG. 13A shows that the proteins were completely separated within 300 seconds. The graph of Log molecular weight versus the inverse migration time, displayed in FIG. 13B, shows a linear correlation with an $R^2$ value of 0.996, which demonstrates the efficiency of the separation. Furthermore, the proteins can elute from the chip and be deposited onto a moving membrane (as shown in FIG. 11). FIG. 14 shows a fluorescent scan of a membrane that was moving at 6 mm/min as it captured proteins that eluted from a chip. According to the scan, the proteins were separated, and successfully deposited onto the membrane.

Effectiveness of the post-column channel in controlling band broadening can be assessed by comparing results on the blot to on-column detection and by imaging the post-column channel during zone elution; for example, the resulting blot can be compared with a blot made using a capillary system as shown in FIG. 1. As shown in FIG. 15, little post-column broadening occurs by using the system shown in FIG. 12.

On-chip detection following post-column dilution can yield protein separations in about 45 s with 70 k to 120 k plates. The high speed of separation by the microfluidic electrophoresis and blotting system represents another difference between the microfluidic approach compared to the capillary approach. In some cases, an improvement in LOD can be achieved in comparison to the capillary system (e.g., up to about 1 order of magnitude improvement) as band broadening across the blotting membrane can be minimized by using the post-column channel design.

The microfluidic electrophoresis and blotting system can further include the following aspects. Methanol and/or SDS-free buffer can be added via the post-column channel, where such solutions can promote the dissociation of SDS from protein (when the sample includes SDS-protein complexes) and enhance binding to the membrane. Flow of electrophoresis buffer or gel from the post-column channel can be achieved using pressure driven flow or electroosmotic flow. For example, a variety of pumps can be used to produce pressure driven flow.

Another aspect includes shaping the outer edge of the chip to facilitate transfer from the post-column outlet to the membrane. Capillary action and/or electric field effects at the edge of the chip may promote some spreading of the sample (e.g., protein) before the sample is trapped by the membrane. Various shapes can be formed on the outside of the chip, such as the pointed end of the chip at the post-column channel outlet shown in FIGS. 11 and 12. Points and sharper edges (as compared to a blunt edge) on the chip may allow for improved protein transfer. In some embodiments, the post-column channel can be fabricated to terminate at the corner of the chip, thereby utilizing a preexisting point or sharp edge of the chip. Another option is to use a capillary extending from the chip as a conduit from the chip to the membrane. Glass chips containing microfluidic channels can be prefabricated with points or tips at the channel outlet(s) or these features can be machined post-fabrication.

One means to evaluate the present microfluidic systems is to compare on-column and on-membrane peak shapes. High resolution confocal microscopy can also be used to examine sample (e.g., fluorescent protein) zones captured on the membrane. For example, various gel imagers use confocal optics, but have a resolution limit of 10 μm and are not designed for Z-axis scanning (i.e., gathering images at different depths). Lateral resolution of such imagers is sufficient for most zones created by the present systems, but it may not be sufficient for some smaller zones created from the chip-based systems. Protein concentration profiles on and inside the membrane may be better characterized by using a confocal microscope. By examining protein zones at high resolution in three dimensions as a function of electric field, various aspects of the present systems. In this manner, electrophoresis buffers or gel solutions used in the post-column channel, electrophoresis buffers or gel solution flow rates, stage translation velocities, sample loading, and membrane wetting solutions can be evaluated and tailored to adjust how a sample is spreading prior to capture on the blotting membrane which can lead to band broadening. For example, zone shape, capture efficiency, and penetration into the membrane may be modified in certain aspects. The chip shown in FIG. 12 was evaluated by loading FITC-BSA into the chip and comparing the peak width in the electrophoresis channel (on-chip), 300 μm into the post-column channel, and on a membrane moving at 3 mm/min. The results, shown in FIG. 15, show minimal band broadening as the protein traversed the system.

The microfluidic systems described herein offer several opportunities to improve the throughput of the traditional Western blot. As already mentioned, the separation itself is much faster. To assay several samples rapidly, the microfluidic chip can be fabricated with multiple sample reservoirs interfaced to the same separation channel. Each sample can be injected and separated sequentially. In this case, the separation "tracks" can be laid down one after the other on a single membrane. A sequence of several samples can therefore be separated in a few minutes (e.g., 8 samples in about 10 min with one sample being a size calibration ladder). The samples can then be treated simultaneously in an immunoassay; e.g., an immunoassay requires about 30 min using a Snap i.d. system (Millipore, Billerica, Mass.). Another approach to improve throughput is to use a set of parallel channels to simultaneously separate several samples. By setting up a system with 8 channels, for example, each requiring 1 min separation, up to 480 samples can be separated in about 1 h, which can all be assayed simultaneously in 30 min using an immunoassay.

Another method for improving throughput comprises performing multiple injections through a single channel. A stage can move a membrane in order to receive separated samples form a microfluidic chip in one or two dimensions. FIG. 16 shows an exemplary chip-based high-throughput system with multiple "tracks" on a single membrane. The membrane can be scanned for fluorescence if the samples are labeled, subjected to a western blot, or both. For example, carbonic anhydrase II (CAII) was mixed with labeled standards (FITC-BSA and FITC-lysozyme) to form a mixture, and injected three times on the chip shown in FIG. 12 with 2 minute intervals between the injections. The electric field applied was 340 V/cm and the membrane was moving at 3.5 mm/min. The samples were deposited on a membrane in a single dimension. After the contents of the third injection eluted onto the moving membrane, the membrane was subjected to both a fluorescent scan, and a western blot with an anti-CAII primary antibody, and a Snap I.d.® Protein Detection System from Millipore. The results of the separation are displayed in FIG. 17, in which the panel A shows the fluorescent scan, and the panel B shows the western blot. The alignment of the images demonstrates that the mixture was successfully separated after each of the three injections, and that the separations were efficient and reproducible.

In some embodiments, throughput can be further increased by performing a detection assay, such as an immunoassay, in-line with the separation. For example, an immunoassay can include treating the blot sequentially with blocking agent, antibody, rinse, secondary antibody (e.g., labeled for fluorescence or chemiluminescence), and a final rinse. The time required for these steps is often limited by the need to rinse chambers and manipulate the blotting membrane. One way to avoid these times is to automatically add the reagents while the separation and blotting is on-going, which can be done using a system such as the one shown in FIG. 18. In this approach, the blotting membrane can be moved past the chip from right to left (direction shown by the arrow), or alternatively the chip can be moved along the membrane from left to right (not shown). As sample (e.g., protein) electrophoreses and elutes from the chip it can be bound to the blotting membrane. Each solution in the detection assay can then be laid over the same track in succession by dispensing from the appropriate channel(s); see channels leading to reservoirs labeled 1, 2, 3, and 4 in FIG. 18. The timing for each addition can be controlled by the translational rate of the membrane and/or the spacing between the channels. The amount of solution delivered can depend on the flow rate (e.g., generated by pressure or voltage) and the size of the channel. Using this system, a single Western blot can be completed in about the same time scale as the separation; e.g., about 1 min. This can be advantageous for analyses which require a quick readout rather than high throughput; e.g., some clinical assays or for monitoring a bioreactor product.

The present systems can deliver individual assay results in minutes with potential for much higher throughput for a larger number of samples. Mass detection limits can also be improved beyond the tens of picograms detected in the examples provided herein. The system offers a substantial improvement in throughput and sensitivity compared to traditional Western blots and uses an easily automated package. The high-throughput aspects are useful in clinical assays or for monitoring biotechnological processes. The excellent mass sensitivity allows rapid microscale analyses not previously attained for electrophoresis and blotting systems, such as traditional Western blotting systems and methods.

In some embodiments, the present systems and methods can be used to resolve various samples, including a sample comprising one or more proteins, SDS-protein complexes, nucleic acids such as DNA or RNA, or any charged molecules or charged complexes that can move through a sieving medium in response to an electric field.

The present systems, apparatus, and methods have many more applications than those described and illustrated here. For example, as protein pharmaceuticals become more common, new methods of characterizing them must be developed. Techniques like peptide mapping (i.e., enzymatic digestion followed by separation of the peaks), affinity binding, and Western blotting are commonly used; however, throughput and sensitivity can be limiting. Proteomics labs also routinely use such methods. The benefits of the present systems make them an attractive choice to use in such applications.

As an example, the present systems, apparatus, and methods can be used to determine proteins released from embryos. Embryo development is dependent upon secreting protein signals that interact with receptors locally and in the placental environment. Understanding the role of these signals is a fundamental challenge. Assays for these proteins can also contribute to improved safety and efficiency of assisted reproduction technology (ART) in both humans and agricultural animals. For ART, embryos are graded by appearance and the "best" embryos are implanted. Visual grading does not have a high predictive value and <30% of the embryos implanted develop normally, creating significant complications. As a result, there is substantial interest in developing non-invasive tests that can predict embryo viability. One approach would be to measure a diagnostic protein in the extracellular fluid from the embryo. Developing such tests requires knowledge of the proteins that are released and assays that are sensitive enough to detect them. The present miniaturized Western blot systems and methods can provide the tools to do this.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms, and that neither should be construed to limit the scope of the disclosure. In some example embodiments, well-known processes, well-known device structures, and well-known technologies are not described in detail. Equivalent changes, modifications and variations of some embodiments, materials, compositions and methods can be made within the scope of the present technology, with substantially similar results.

The following non-limiting discussion of terminology is provided with respect to the present technology.

The headings (such as "Introduction" and "Summary") and sub-headings used herein are intended only for general organization of topics within the present disclosure, and are not intended to limit the disclosure of the technology or any aspect thereof. In particular, subject matter disclosed in the "Introduction" may include novel technology and may not constitute a recitation of prior art. Subject matter disclosed in the "Summary" is not an exhaustive or complete disclosure of the entire scope of the technology or any embodiments thereof. Classification or discussion of a material within a section of this specification as having a particular utility is made for convenience, and no inference should be drawn that the material must necessarily or solely function in accordance with its classification herein when it is used in any given composition.

The description and specific examples, while indicating embodiments of the technology, are intended for purposes of illustration only and are not intended to limit the scope of the technology. Moreover, recitation of multiple embodiments having stated features is not intended to exclude other embodiments having additional features, or other embodiments incorporating different combinations of the stated features. Specific examples are provided for illustrative purposes of how to make and use the compositions and methods of this technology and, unless explicitly stated otherwise, are not intended to be a representation that given embodiments of this technology have, or have not, been made or tested.

As used herein, the words "desire" or "desirable" refer to embodiments of the technology that afford certain benefits, under certain circumstances. However, other embodiments may also be desirable, under the same or other circumstances. Furthermore, the recitation of one or more desired embodiments does not imply that other embodiments are not useful, and is not intended to exclude other embodiments from the scope of the technology.

As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present technology that do not contain those elements or features.

Although the open-ended term "comprising," as a synonym of non-restrictive terms such as including, containing, or having, is used herein to describe and claim embodiments of the present technology, embodiments may alternatively be described using more limiting terms such as "consisting of" or "consisting essentially of." Thus, for any given embodiment reciting materials, components or process steps, the present technology also specifically includes embodiments consisting of, or consisting essentially of, such materials, components or processes excluding additional materials, components or processes (for consisting of) and excluding additional materials, components or processes affecting the significant properties of the embodiment (for consisting essentially of), even though such additional materials, components or processes are not explicitly recited in this application. For example, recitation of a composition or process reciting elements A, B and C specifically envisions embodiments consisting of, and consisting essentially of, A, B and C, excluding an element D that may be recited in the art, even though element D is not explicitly described as being excluded herein.

As referred to herein, all compositional percentages are by weight of the total composition, unless otherwise specified. Disclosures of ranges are, unless specified otherwise, inclusive of endpoints and include all distinct values and further divided ranges within the entire range. Thus, for example, a range of "from A to B" or "from about A to about B" is inclusive of A and of B. Disclosure of values and ranges of values for specific parameters (such as temperatures, molecular weights, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that Parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if Parameter X is exemplified herein to have values in the range of 1-10, or 2-9, or 3-8, it is also envisioned that Parameter X may have other ranges of values including 1-9, 1-8, 1-3, 1-2, 2-10, 2-8, 2-3, 3-10, and 3-9.

"A" and "an" as used herein indicate "at least one" of the item is present; a plurality of such items may be present, when possible. "About" when applied to values indicates that the calculation or the measurement allows some slight imprecision in the value (with some approach to exactness in the value; approximately or reasonably close to the value; nearly). If, for some reason, the imprecision provided by "about" is not otherwise understood in the art with this ordinary meaning, then "about" as used herein indicates at least variations that may arise from ordinary methods of measuring or using such parameters.

When an element or layer is referred to as being "on," "engaged to," "connected to" or "coupled to" another element or layer, it may be directly on, engaged, connected or coupled to the other element or layer, or intervening elements or layers may be present. In contrast, when an element is referred to as being "directly on," "directly engaged to," "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

What is claimed is:

1. A capillary electrophoresis and blotting system comprising:
   an electrophoresis component comprising a separation capillary having proximal and distal ends, the separation capillary operable to be filled with a sieving medium and electrophorese a sample from the proximal end to the distal end;
   a blotting component comprising a surface;
   a translating component operable to change position of the distal end of the separation capillary relative to the surface of the blotting component, wherein the distal end of the separation capillary and the surface of the blotting component are operable to be electrically coupled during electrophoresis of the sample; and
   a buffer capillary having proximal and distal ends, the distal end of the buffer capillary located proximate to the distal end of the separation capillary, wherein the buffer capillary is operable to be filled with electrophoresis buffer or gel to electrically couple the distal end of the separation capillary and the surface of the blotting component during electrophoresis of the sample.

2. The system of claim 1, wherein the separation capillary comprises the sieving medium.

3. The system of claim 2, wherein the sieving medium comprises polyacrylamide.

4. The system of claim 1, wherein the buffer capillary comprises the electrophoresis buffer or gel.

5. The system of claim 1, further comprising a pump operable to pump electrophoresis buffer or gel from the proximal end to the distal end of the buffer capillary.

6. The system of claim 1, wherein the buffer capillary comprises a sheath capillary coaxial to the separation capillary.

7. The system of claim 6, wherein the distal end of the buffer capillary extends further than the distal end of the separation capillary toward the surface of the blotting component.

8. The system of claim 1, wherein the surface of the blotting component comprises a blotting membrane.

9. The system of claim 8, wherein the blotting membrane comprises polyvinylidene fluoride, nitrocellulose, or nylon.

10. The system of claim 8, further comprising a wick operable to wet the blotting membrane.

11. The system of claim 8, wherein the blotting membrane comprises a gel impregnated membrane.

12. The system of claim 1, wherein the electrophoresis component further comprises a plurality of separating capillaries.

13. The system of claim 1, further comprising an assay component comprising a reagent capillary having proximal and distal ends, the reagent capillary operable to be filled with a reagent and dispense the reagent from the distal end.

14. The system of claim 13, wherein the distal end of the reagent capillary is operable to follow the distal end of the separation capillary when position of the distal end of the separation capillary is changed by the translation component.

15. The system of claim 13, wherein the assay component comprises a plurality of reagent capillaries including a first reagent capillary and a second reagent capillary.

16. The system of claim 15, wherein the distal end of the first reagent capillary is operable to follow the distal end of the separation capillary when position of the distal end of the separation capillary is changed by the translation component and the distal end of the second reagent capillary is operable to follow the distal end of the first reagent capillary.

17. The system of claim 16, wherein the first reagent capillary comprises a blocking reagent and the second reagent capillary comprises a detecting reagent.

18. A capillary electrophoresis and blotting method comprising:
providing an electrophoresis and blotting system according to claim 1, wherein the separation capillary comprises a sieving medium and the surface of the blotting component comprises a blotting membrane; and
electrophoresing a sample through the separation capillary from the proximal end to the distal end and using the translating component to change position of the distal end of the separation capillary relative to the surface of the blotting component.

19. The method of claim 18, wherein the sample comprises a protein.

20. The method of claim 19, further comprising detecting the protein on the blotting membrane.

21. A microfluidic electrophoresis and blotting system comprising:
an electrophoresis component comprising a microfluidic channel and a post-column channel, the microfluidic channel having proximal and distal ends and operable to be filled with a sieving medium and electrophorese a sample from the proximal end toward the distal end, the post-column channel having proximal and distal ends and operable to be filled with an electrophoresis buffer or gel, wherein the distal end of the microfluidic channel is coupled to the proximal end of the post-column channel;
a blotting component comprising a surface, wherein the surface of the blotting component comprises a blotting membrane; and
a translating component operable to change position of the distal end of the post-column channel relative to the surface of the blotting component, wherein the distal end of the post-column channel and the surface of the blotting component are operable to be electrically coupled during electrophoresis of the sample.

22. The system of claim 21, further comprising a post-column addition solution reservoir coupled at the distal end of the microfluidic channel and the proximal end of the post-column channel, the post-column addition solution reservoir operable to be filled with an electrophoresis buffer or gel.

23. The system of claim 22, further comprising a pump operable to pump electrophoresis buffer or gel from the post-column addition solution reservoir to the proximal end of the post-column channel, through the post-column channel, and to the distal end of the post-column channel.

24. The system of claim 21, wherein the microfluidic channel comprises the sieving medium.

25. The system of claim 24, wherein the sieving medium comprises polyacrylamide.

26. The system of claim 21, wherein the blotting membrane comprises polyvinylidene fluoride, nitrocellulose, or nylon.

27. The system of claim 21, wherein the electrophoresis component comprises a glass chip comprising the microfluidic channel and the post-column channel.

28. The system of claim 21, wherein the distal end of the post-column channel is closer to the surface of the blotting component than any other portion of the electrophoresis component.

29. The system of claim 21, wherein the electrophoresis component further comprises a plurality of microfluidic channels and a plurality of post-column channels.

30. The system of claim 21, further comprising an assay component comprising a reagent reservoir operable to be filled with a reagent and dispense the reagent to the surface of the blotting component.

31. The system of claim 30, wherein the reagent reservoir is operable to dispense the reagent to a position on the surface of the blotting component that follows the distal end of the post-column channel when position of the distal end of the post-column channel is changed by the translation component.

32. The system of claim 30, wherein the assay component comprises a plurality of reagent reservoirs operable to be filled with a plurality of reagents and dispense the reagents to the surface of the blotting component, the plurality of reagent reservoirs including a first reagent reservoir and a second reagent reservoir.

33. The system of claim 32, wherein the first reagent reservoir is operable to dispense reagent to a first position on the surface of the blotting component that follows the distal end of the post-column channel when position of the distal end of the post-column channel is changed by the translation component and the second reagent reservoir is operable to dispense reagent to a second position on the surface of the blotting component that follows the first position.

34. The system of claim 33, wherein the first reagent reservoir comprises a blocking reagent and the second reagent capillary comprises a detecting reagent.

35. A microfluidic electrophoresis and blotting method comprising:
providing a microfluidic electrophoresis and blotting system according to claim 21, wherein the microfluidic channel comprises a sieving medium, the post-column channel comprises an electrophoresis buffer or gel, and the surface of the blotting component comprises a blotting membrane; and electrophoresing a sample through the microfluidic channel from the proximal end toward the distal end, through the post-column channel from the proximal end toward the distal end, and toward the surface of the blotting component and the blotting membrane, and using the translating component to change position of the distal end of the post-column channel relative to the surface of the blotting component.

36. The method of claim 35, wherein the sample comprises a protein.

37. The method of claim 36, further comprising detecting the protein on the blotting membrane.

38. The method of claim 37, wherein the detecting comprises an immunoassay.

* * * * *